(12) United States Patent
van Reis

(10) Patent No.: US 7,153,426 B2
(45) Date of Patent: Dec. 26, 2006

(54) CHARGED FILTRATION MEMBRANES AND USES THEREFOR

(75) Inventor: Robert D. van Reis, Redwood City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 11/241,279

(22) Filed: Sep. 29, 2005

(65) Prior Publication Data

US 2006/0157412 A1 Jul. 20, 2006

Related U.S. Application Data

(60) Division of application No. 10/417,715, filed on Apr. 16, 2003, now Pat. No. 7,001,550, which is a continuation-in-part of application No. 09/621,242, filed on Jul. 21, 2000, now abandoned.

(60) Provisional application No. 60/146,558, filed on Jul. 30, 1999.

(51) Int. Cl.
*B01D 39/00* (2006.01)
*B01D 39/14* (2006.01)
*B01D 29/00* (2006.01)

(52) U.S. Cl. .............................. 210/500.29; 210/500.3; 210/500.31; 210/500.32; 210/490; 210/645

(58) Field of Classification Search ............ 210/500.27, 210/500.29, 500.3, 500.31, 500.32, 490, 210/500.37, 645, 502.1; 264/48
See application file for complete search history.

(56) References Cited

U.S. PATENT DOCUMENTS

| | | | |
|---|---|---|---|
| 4,604,204 A * | 8/1986 | Linder et al. ............... | 210/490 |
| 4,604,208 A * | 8/1986 | Chu et al. .................. | 210/636 |
| 5,136,032 A * | 8/1992 | Nagamatsu et al. ........ | 536/18.7 |
| 5,522,991 A | 6/1996 | Tuccelli et al. ............. | 210/490 |
| 5,925,552 A * | 7/1999 | Keogh et al. ............... | 435/174 |
| 6,617,142 B1 * | 9/2003 | Keogh et al. ............... | 435/174 |
| 6,884,842 B1 * | 4/2005 | Soane et al. ............... | 525/54.1 |

FOREIGN PATENT DOCUMENTS

GB 1504261 * 3/1968

OTHER PUBLICATIONS

Millesime, et al., "Fractionation of Proteins with Modified Membranes" *Bioseparation* 6: pp. 135-145, 1996.
Millesime, et al., "Ultrafiltration of Lysozyme and Bovine Serum Albumin with Polysulfone Membrane Modified with Quanternized Polyvinylimidazole", *Journal of Membrane Science* 89: pp. 223-234 (1994).
Miyama, et al., "Charged Ultrafiltration Membrane for Permeation of Proteins", *Journal of Applied Polymer Science*, vol. 36, pp. 925-933 (1988).
Nakao, et al., "Separation of Proteins by Charged Ultrafiltration Membranes", *Desalination* 70: pp. 191-205 (1988).

(Continued)

*Primary Examiner*—Ana Fortuna
(74) *Attorney, Agent, or Firm*—Deirdre L. Conley; Ginger R. Dreger, Esq.; Heller Ehrman LLP

(57) ABSTRACT

The invention relates to charged filtration membranes and their use for separation of a protein from solvent, low molecular weight solutes or a mixture of proteins. Modification of the membranes to generate charge includes modification of membrane pores to alter charge within a pore and alter the size of a pore. Consequently, the protein is separated from other solutes in a mixture based on size as well as net protein charge and membrane charge.

11 Claims, 11 Drawing Sheets

OTHER PUBLICATIONS

Tkacik, et al., "A rejection profile test for ultrafiltration membranes & devices", Biotechnology, vol. 9, pp. 941-946, (1991).

van Reis, et al., "High performance tangential flow filtration", Biotechnology and Bioengineering, vol. 56, No. 1, pp. 71-82, (1997).

van Reis, et al., "High-performance tangential flow filtration using charged membranes", Journal of Membrane Science, vol. 159, pp. 133-142, (1999).

van Reis, et al., "Protein ultrafiltration", Encyclopedia of Bioprocess Technology: Fermentation, Biocatalysis, and Bioseparation, vol. 4, John Wiley & Sons, Inc., pp. 2197, (1999).

Zerman, et al., "Microfiltration and Ultrafiltration: Principles and Applications", Marcel Dekker, Inc., pp. 3 (1996).

Zerman, et al., "Microfiltration and Ultrafiltration: Principles and Applications", Marcel Dekker, Inc., pp. 299-301 (1996).

Zerman, et al., "Microfiltration and Ultrafiltration: Principles and Applications", Marcel Dekker, Inc., pp. 308 (1996).

* cited by examiner

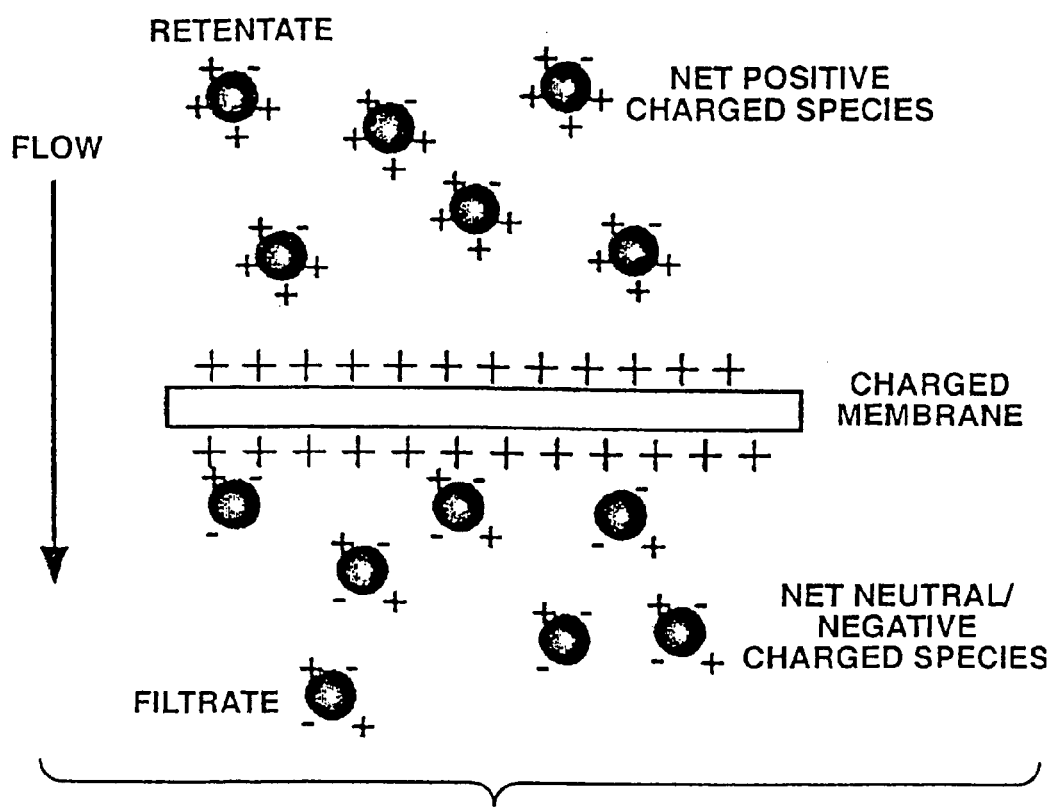
FIG._1
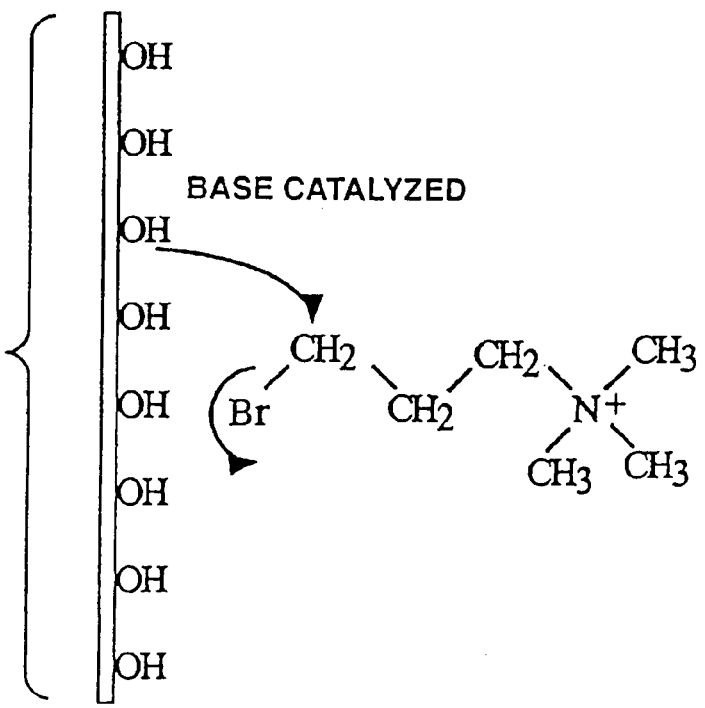
FIG._2A

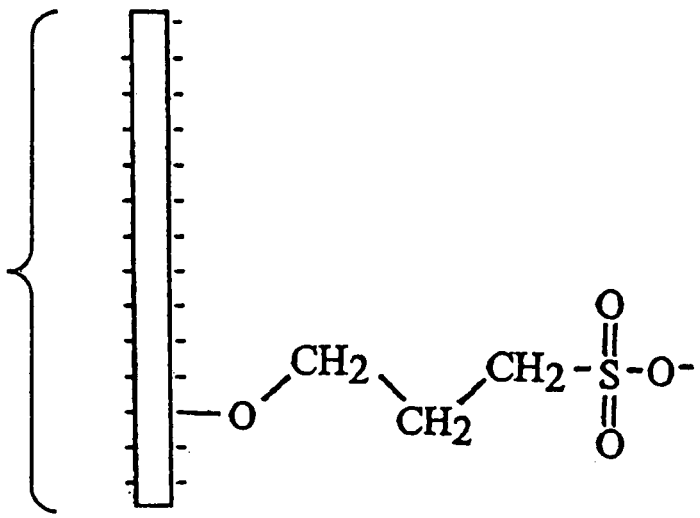
FIG._2B
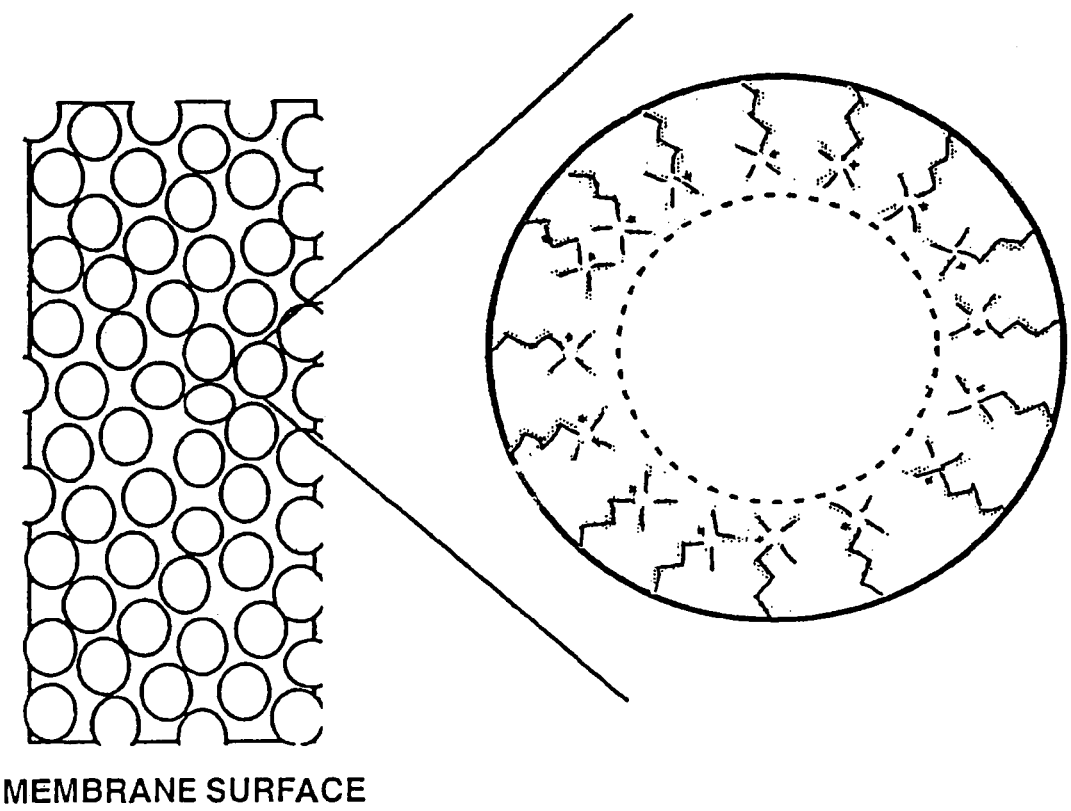
MEMBRANE SURFACE
FIG._3

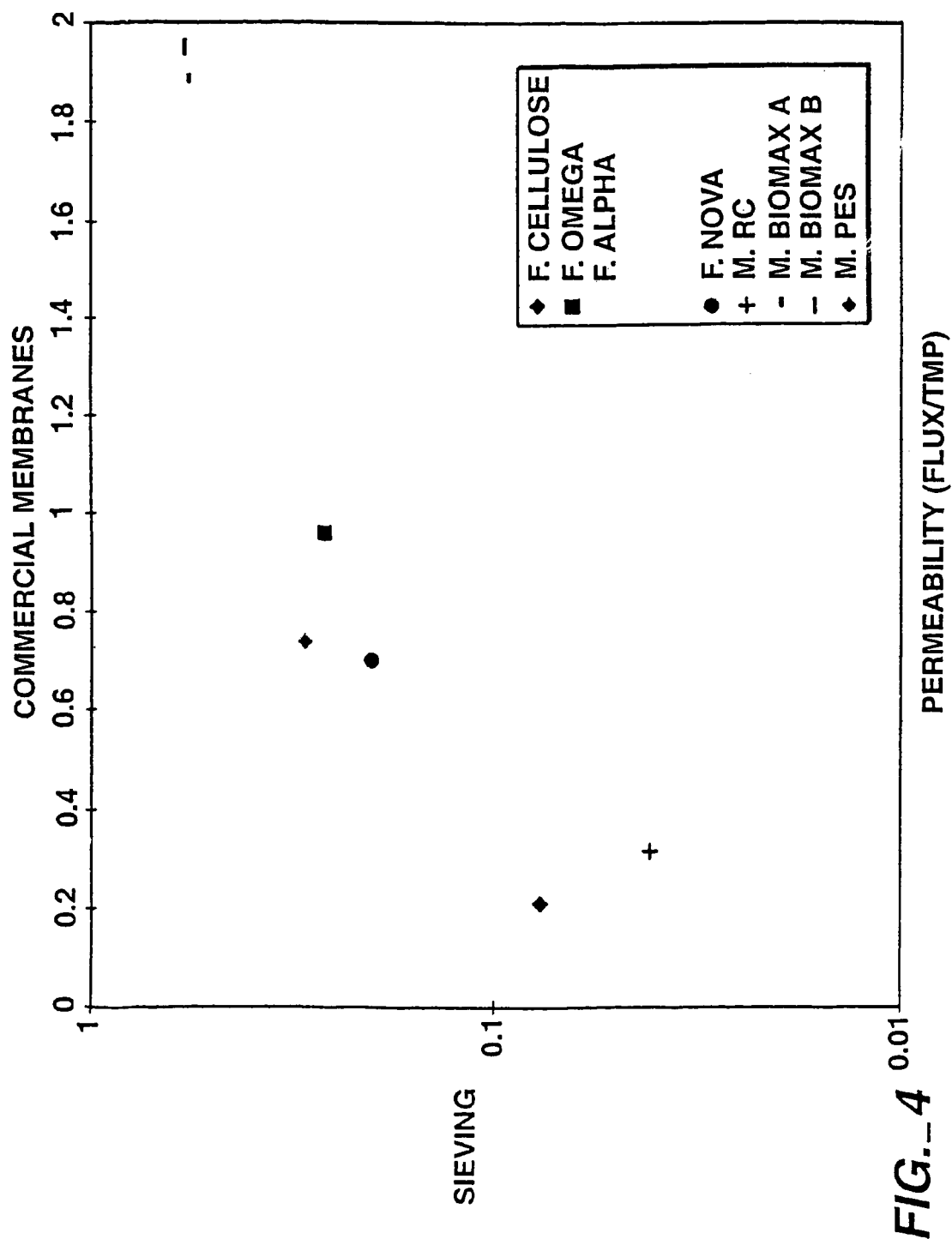
FIG._4

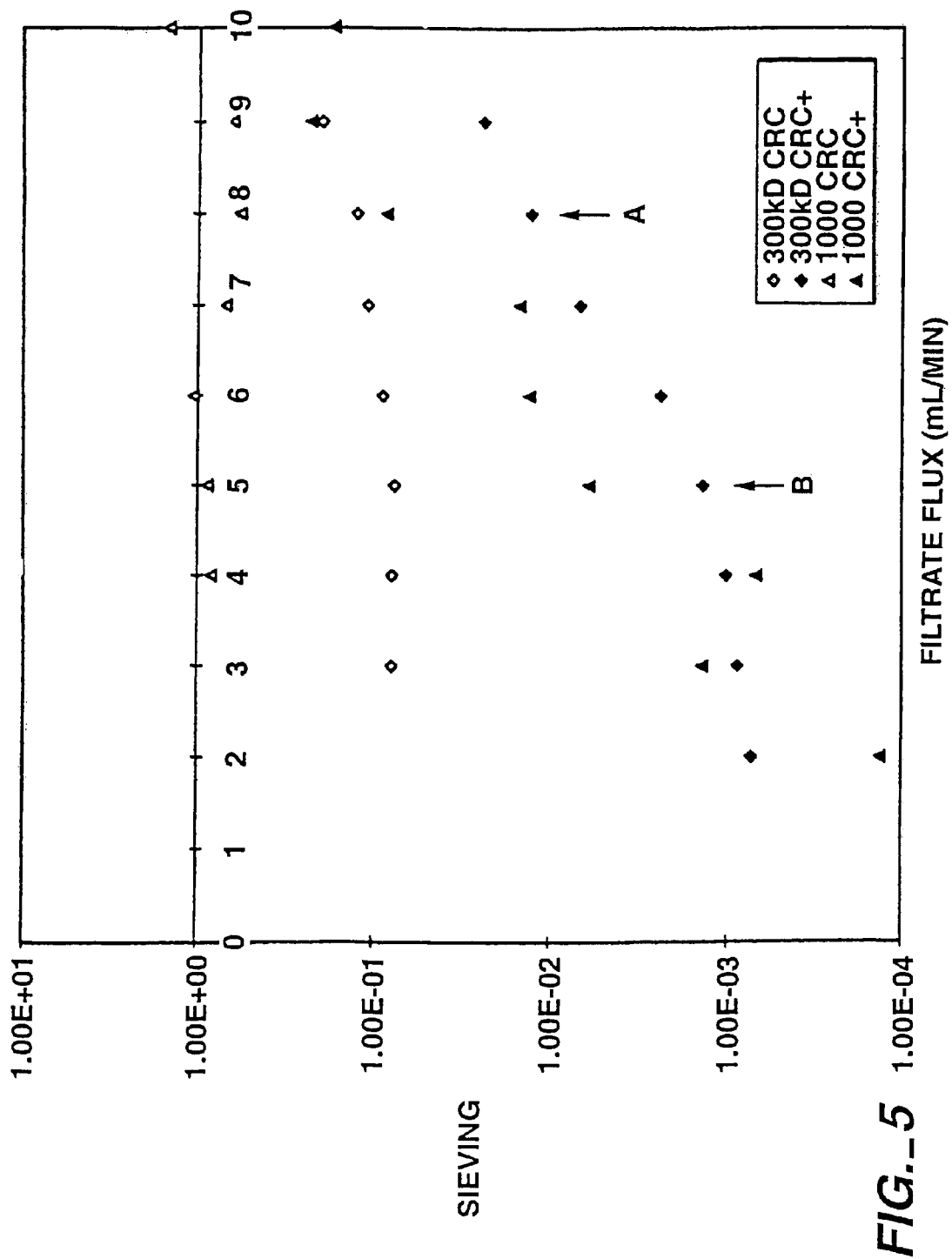
FIG._5

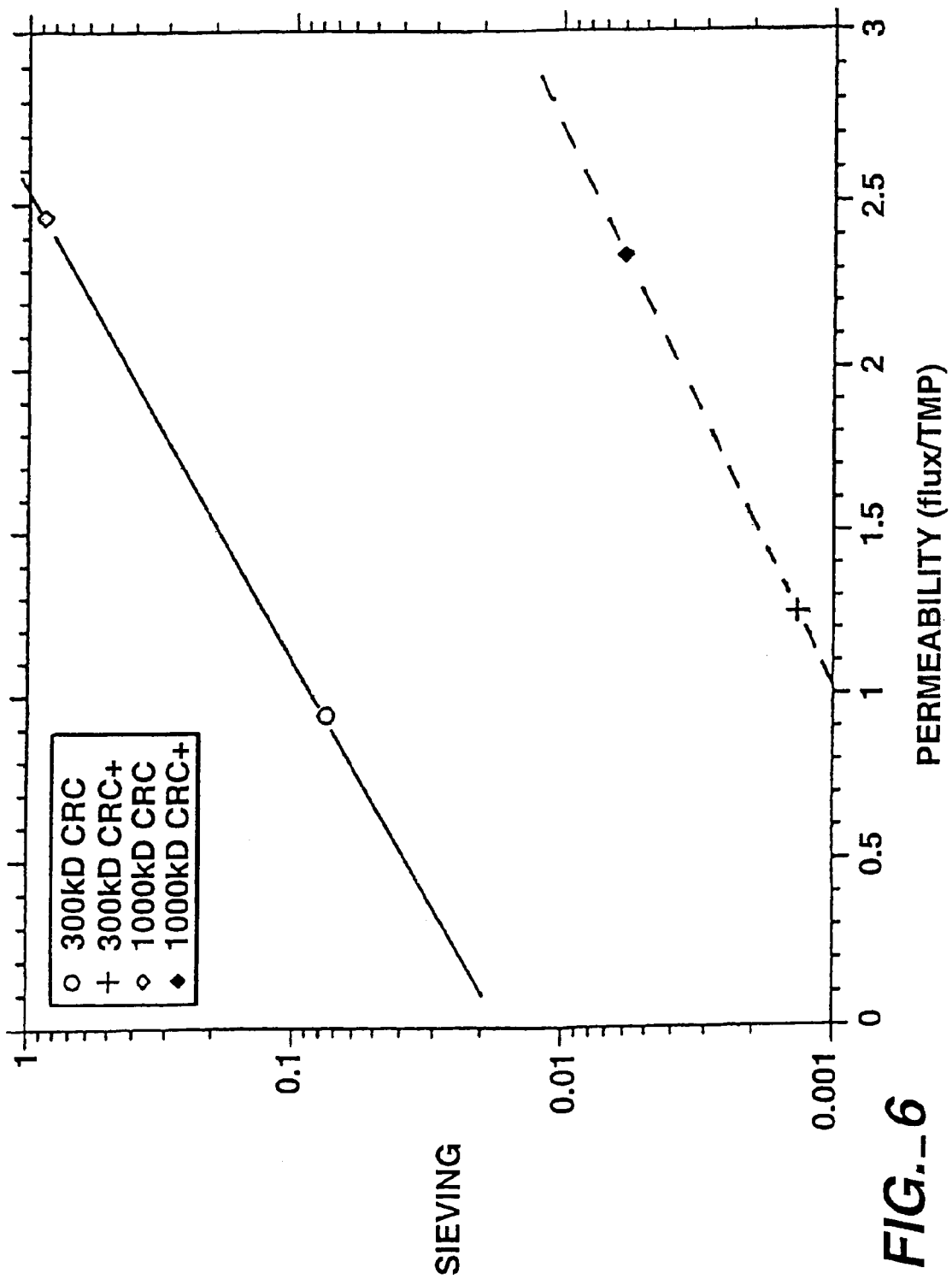
FIG._6

CHARGED FILTRATION MEMBRANES AND USES THEREFOR

RELATED APPLICATIONS

This application is a divisional application of application Ser. No. 10/417,715 filed Apr. 16, 2003, now U.S. Pat. No. 7,001,550, which is a continuation-in-part of application Ser. No. 09/621,242 filed Jul. 21, 2000 (now abandoned), which claims priority under 35 USC 119(e) to provisional application No. 60/146,558 filed Jul. 30, 1999, the contents of which are incorporated herein by reference.

FIELD OF THE INVENTION

The invention relates to charged filtration membranes and their use for separation of a protein from solvent, low molecular weight solutes or a mixture of proteins. Modification of the membranes to generate charge includes modification of membrane pores to alter charge within a pore and alter the size of a pore. Consequently, the protein is separated from other solutes in a mixture based on size as well as net protein charge and membrane charge.

BACKGROUND OF THE INVENTION

A filtration membrane useful for protein separations is a synthetic (frequently polymeric) selective barrier for industrial or lab-scale microfiltration (MF) or ultrafitration (UF) (see Leos J. Zeman and Andrew L. Zydney, "Microfiltration and Ultrafiltration: Principles and Applications," 1996, Marcel Dekker, Inc., p. 3). In these processes, certain feed stream components, such as proteins, pass through pores of the membrane into a filtrate, while other, usually larger, proteins or components are retained by the membrane in the retentate (see Zeman and Zydney, supra, p. 3).

Protein ultrafiltration is a pressure-driven membrane process used for the concentration or purification of protein solutions (Robert van Reis and Andrew L. Zydney, "Protein Ultrafiltration" in *Encyclopedia of Bioprocess Technology: Fermentation, Biocatalysis, and Bioseparation*, M. C. Flickinger and S. W. Drew, eds., John Wiley & Sons, Inc. (1999), p. 2197). UF membranes typically have a mean pore size between 10 and 500 Angstroms, which is between the mean pore size of reverse osmosis and microfiltration membranes. Ultrafiltration separates solutes based on differences in the rate of filtration of different components across the membrane in response to a given pressure driving force (R. van Reis and A. L. Zydney, supra, p. 2197). Solute filtration rates, and thus membrane selectivity, are determined by both thermodynamic and hydrodynamic interactions (R. van Reis and A. L. Zydney, supra, p. 2197). Ultrafiltration is frequently used in downstream processing for protein concentration, buffer exchange and desalting, protein purification, virus clearance, and clarification (R. van Reis and A. L. Zydney, supra, p. 2197).

Protein purification is also accomplished using high-performance tangential flow filtration (HPTFF), with the desired protein collected in either the retentate or filtrate depending on the relative filtration rates (R. van Reis and A. L. Zydney, supra, p. 2197). HPTFF is useful for separating proteins of similar size using semipermeable membranes (See, for example, R. van Reis, et al., Biotech. Bioeng. 56:71–82 (1997) and R. van Reis et al., J. Memb. Sci. 159:133–142 (1999)). HPTFF achieves high selectivity by controlling filtrate flux and device fluid mechanics in order to minimize fouling and exploit the effects of concentration polarization (R. van Reis et al., J. Memb. Sci. 159:133–142 (1999)).

Despite the value of these advanced filtration methods, there is a need for improved filtration membrane characteristics such that separation speed may be increased without sacrificing membrane selectivity or speed. Such improvements would reduce cost of separation and increase yield of valuable proteins.

SUMMARY OF THE INVENTION

The invention relates to filtration membranes possessing a net charge, either positive or negative, and further relates to methods of making the charged membranes and using them in the separation of a protein from a solute or mixture of solutes, such as salts, buffer solutes, or proteins. The proteins are separated based, in part, on the size of the proteins and, in part, on the net charge of the proteins. The charged membranes repel proteins having the same charge polarity as the membrane, thereby retaining such proteins on the upstream side of the membrane. Proteins pass through the membrane pores if they have a net neutral charge or a polarity opposite that of the membrane and are smaller than the average pore diameter. The sieving property of the charged membranes of the invention, measured as the sieving coefficient, is dramatically improved relative to an uncharged membrane, as illustrated by a shift in a plot of permeability (Lp) versus sieving (S) from higher sieving values for neutral membranes to lower sieving values for charged membranes having the same charge polarity as the protein or other solute of interest retained by the charged membrane (see FIGS. 6–11). According to the invention, a reduction in sieving for solute and membrane of like charge polarity is greater than any reduction (if any) in membrane permeability such that a graph of permeability (Lp) versus sieving (S) shifts to lower sieving values (FIGS. 6–11).

Conventional protein filtration balances membrane permeability with solute sieving. Ideally, permeability is high to allow rapid separation, while sieving is low for selective retention of the desired protein. Using conventional filtration membranes, however, one of ordinary skill in the art sacrifices permeability to gain selectivity, thereby limiting separation speed and protein recovery, respectively. The charged membranes of the invention, on the other hand, provide high permeability, thereby speeding separation, while lowering sieving for more selective separation and higher yield of the desired protein.

In one aspect, the invention involves a filtration membrane covalently modified with a charged compound or a compound capable of being chemically modified to possess a charge. The filtration membrane may be any membrane including, but not limited to, cellulose, cellulose diacetate and triacetate, cellulose nitrate, and cellulose diacetate/cellulose nitrate blends. Filtration membranes are commercially available from various sources including, but not limited to, Millipore Corp., Bedford, Mass., and Pall Corp., Happauge, N.Y. Preferably the filtration membrane has hydroxyl groups available on the membrane surface for reaction with a derivatizing compound. Preferably the hydroxyl groups are primary alcohol moieties, such as those of a cellulose matrix. Preferably, the membrane is regenerated cellulose, more preferably the membrane is composite regenerated cellulose (CRC) (See, for example, U.S. Pat. No. 5,522,991 for a description of cellulosic membranes.) A cellulose membrane has the advantages of inherent low fouling characteristics, hydrophilicity, the availability of primary alcohol groups (from the glucose moieties of cellulose) for reaction with a charged compound, and stability under alkaline conditions. A CRC membrane has the additional advantage of mechanical strength.

In one embodiment, the membrane is a cellulose membrane, preferably a CRC membrane, modified to have a net charge (positive or negative), wherein the permeability versus sieving performance is enhanced (shifted to lower sieving values where the solute and charged membrane have like charge polarity) as illustrated by a plot of sieving versus permeability (see FIGS. 6–11). For example, for a given membrane permeability, the sieving coefficient is decreased by at least 1.5 fold, alternatively at least 5 fold, at least 10 fold, at least 20 fold, at least 50 fold, or at least 100 fold relative to the sieving value of an uncharged membrane for a protein retained on the upstream side of the membrane when the membrane and retained protein have like charge polarity (positive or negative).

In another embodiment, the invention involves a membrane, preferably a CRC membrane, in which a plurality of the hydroxyl or primary alcohol groups are covalently linked to a charged compound. Preferably, the charged compound retains its charge under the conditions used to separate the protein from solutes or a mixture of proteins.

In another embodiment, the charged compound is positively charged. The positive charge may be generated from any compound that retains its charge under the conditions of protein separation. For example, the charge may be generated by, but not limited to, an amine, a quaternary amine, and the like. Preferably, the charged reactive compound is capable of maintaining its charge polarity under the conditions of protein separation. The amine or other charged lower alkyl groups have from one to 8 carbon atoms, although the number of alkyl groups and/or carbon atoms may be varied to achieve solubility in the reaction conditions and/or to react with a pore surface under the steric constraints of the pore. Preferably, the alkyl groups are methyl, ethyl, and propyl groups. For example, the amine moiety of the positively charged compound may be a trialkyl or dialkyl amine, such as trimethyl amine, triethyl amine, diethylamino ethyl, and the like. Listed in Table 1 (see Example 1) are non-limiting examples of useful positively charged reactive compounds for derivatizing a membrane.

In another embodiment, the charged compound is negatively charged. The negative charge may be generated from any compound that retains its charge under the conditions of protein separation. For example, the charge may be generated by, but not limited to, an acid, such as a carboxylic acid, a sulfonic acid, carboxymethyl sulfonate, methyl sulfonate, and the like. The negatively charged moiety may optionally be covalently attached to a chain of alkyl groups of from 1 to 8 or more carbon atoms, although the number of alkyl groups and/or carbon atoms may be varied to achieve solubility in the reaction conditions and/or to react with a pore surface under the steric constraints of the pore. Preferably, the alkyl groups are methyl, ethyl, and propyl groups. Listed in Table 1 (see Example 1) are non-limiting examples of useful negatively charged reactive compounds for derivatizing a membrane.

In still another embodiment, the charged compound comprises a linker arm between the charged moiety and the moiety covalently linked to a reactive group of the membrane. The linker arm comprises a portion of the reactive charged compound between a moiety reactive with the membrane and the charged moiety. Alternatively, a linker arm may be added or extended by reacting a membrane with a linker ligand (see Table 1 for non-limiting examples of linker ligands). A linker ligand is compound comprising a first moiety reactive with the membrane (such as a halide for reactivity with a CRC membrane) and a second moiety reactive with a charged reactive compound (such as a hydroxyl moiety reactive with a halide of a charged reactive compound). Where the membrane is a CRC membrane, the linker arm separates the charged moiety and a hydroxl or primary alcohol group of the cellulosic matrix with which the linker ligand reacts. The linker arm allows the charged moiety to project away from the surface of the membrane. Where the charged compound modifies the surface of a membrane pore, the linker arm allows the compound to project into the lumen of the pore, thereby modifying the size of the pore. Larger membrane pores will be reduced in size, smaller pores are filled, and still smaller pores fail to be penetrated by the compound due to steric hinderance and/or electrostatic repulsion. Consequently, membrane pore size distribution is narrowed, providing improved protein separation.

In another embodiment, the linker arm comprises an alkyl chain of from one to and including twenty carbon atoms. The alkyl chain may be branched and the branch may link a first charged moiety to a second (or additional) charged moiety. The linker arm may be any chain of atoms or molecular moieties that are themselves inert to the reaction conditions used to link the charge to the membrane, and inert to the conditions of protein separation. The length of the linker arm is chosen according to the desired pore size modification. Preferably the linker arm length allows the reactive charged compound to penetrate and react within some of the pores thereby narrowing the pore size distribution. Linker arms may include, but are not limited to, carbohydrates, dextrans, saccharides, peptides (having charged or uncharged amino acid side chains), polymers (such as polyvinyl derivatives, polyether derivatives, and the like), and like chains. Where the filtration membrane is hydrophilic and aqueous reaction conditions are used to link the charged compound to the membrane, the linker arm is preferably hydrophilic and the charged compound in its reactive form (for reaction with the membrane) is soluble in the aqueous reaction solution.

Accordingly, the invention may comprise a linker arm that is an alkyl chain of between one and twenty carbon atoms in length, preferably one to ten, more preferably one to seven carbon atoms. Alternatively, the linker arm may be a carbohydrate or dextran chain of from one to, and including, fifteen saccharide moieties, preferably one to ten, more preferably one to five saccharide moieties. The linker arm may be a peptide of one to twenty five amino acids, preferably one to fifteen, more preferably one to ten amino acids. In addition, the linker arm may be any polymer of from one to twenty five repeat units that is inert to the reaction and separation conditions. The linker arm may be branched, wherein each branch is shorter than the length of the main branch (the linker arm) linked to the reactive group. Each branch may end in a charged moiety and the charge of each charged moiety is the same polarity (either positive or negative).

In an embodiment, the reactive charged compound has the general formula, X-L-Y, where X is a reactive group that reacts with a reactive group on the membrane, L is the linker arm, and Y is the charged group. Accordingly, where the membrane is a CRC membrane and the reactive groups on the membrane are primary alcohol groups, X of the reactive charged compound is a moiety that promotes reaction with the primary alcohol groups under aqueous conditions. As such, X is preferably a leaving group susceptible to nucleophilic attack by a hydroxyl or primary alcohol group to form an ether linkage between the cellulosic carbohydrate matrix and the linker arm of the charged compound. Thus, useful reactive charged compounds are alkyl halides, and the reactive group is a halide including, but not limited to, chloride, bromide, or iodide.

In yet another aspect, the invention involves a method of making a charged membrane of the invention, the method comprising reacting a reactive charged compound with a plurality of reactive sites on the membrane such that the charged portion of the charged compound is covalently linked to the membrane. After reaction, the net charge of the membrane is positive or negative. Preferably, the reactive charged compound penetrates a plurality of membrane pores and modifies the pore size distribution. Preferably, the pore size distribution is narrowed.

In an embodiment, the method of the invention comprises a reactive charged compound that is uncharged during the covalent attachment to the membrane and is later reacted to create the charge (either positive or negative) that generates the net charge for the membrane. The reactive charged compound may be added to the end of the linker arm (or branches) after the linker arm is covalently attached to the membrane. Where the charged group is positive, the charged group may be an amine, a quaternary amine, such as a dialkyl or trialkyl, and the like. Where the charged group is negative, the charged group is an acid, such as a sulfonic acid, a carboxylic acid, a carboxymethyl sulfonyl group, and the like. The charged group is chosen as a moiety that will maintain its charge under the conditions of the protein separation method of the invention. A non-limiting list of reactive ligand compounds (where that term is used synonymously with the terms "reactive ligands" and "reactive compounds"), useful for adding positive or negative charge to membrane when covalently attached to it, is provided in Table 1 of Example 1, herein. Also provided in Table 1 is a non-limiting list of linker ligands that may be first reacted with the membrane surface followed by reaction with a charged reactive compound, thereby increasing the distance of the charged moiety from the membrane surface.

In another aspect, the invention involves a filtration membrane derivatization method in which the reactive compound is contacted with the membrane surface and pores by passing the solvent and reactive compound over the membrane surface and through a plurality of pores of the membrane. In an embodiment of the invention in which a linker is added as a first reactive compound followed by the addition of the charged reactive compound as the second reactive compound, the embodiment also includes passage of the first and second reactive compounds through a plurality of membrane pores. Typically, the reactive compound passes from a first exterior side of the membrane to a second exterior side of the membrane. In a further embodiment, the reactive compound is recirculated from the second exterior membrane side to the first exterior membrane side at least once. In still further embodiments, the recirculating occurs multiple times until the reaction is considered complete. The reactive compound may be caused to pass through a plurality of membrane pores by various methods including, but not limited to, introducing positive pressure from the first membrane side such that a positive pressure differential is created between the first and second membrane sides. Positive pressure may be applied using pneumatic or hydraulic pressure. Alternatively, a negative pressure from the second membrane side may be created to create a similar pressure differential. Gravitational or centrifugal force may be used to create a pressure differential across the membrane. Other, standard methods of generating a pressure differential are useful in the present invention.

In another aspect, the invention involves a membrane filtration method for separating a protein from a solute or mixture of solutes (such as salts, buffer solutes, or proteins) using a charged membrane of the invention. Preferably the method involves (1) contacting a protein within a solute mixture with a charged cellulosic membrane, more preferably a CRC membrane that has been reacted with a reactive charged compound to generate a link, via a linker arm, to a charged group, wherein the protein to be retained has a net charge or charge polarity that is the same as the charge polarity of the membrane under the separation conditions, and (2) separating the protein from at least one other solute or protein in the mixture, wherein the other protein is a different size, has a different net charge or charge polarity, or is neutral.

In an embodiment of the invention, prior to contacting a protein within a mixture with the membrane, the pH of the mixture is altered causing the net charge or charge polarity of the desired protein to be the same as the charge polarity as the membrane. At the same time, the pH change renders at least one solute to be separated from the desired protein because the solute is neutral or has a charge opposite the membrane charge, or the solute is larger or smaller than that of the target protein and is differentially retained by the membrane. During the contacting and separating steps, the neutral solute passes through the charged membrane into the filtrate, while the desired charged protein is retained on the upstream side of the membrane. This embodiment of the invention may be repeated to successively remove solutes from the protein mixture.

In an embodiment of the invention, the filtration method is ultrafiltration (see generally, van Reis and Zydney, "Protein Ultrafiltration," supra, p. 2197, for a description of ultrafiltration), wherein the embodiment comprises use of a charged membrane in ultrafiltration for the separation of a solute from a mixture of solutes. Optionally, the solute to be separated by charged membrane ultrafiltration is a polypeptide or protein. In another embodiment of the invention, the filtration method is high-performance tangential flow filtration, HPTFF (see generally, R. van Reis, et al., J. Memb. Sci. 159:133–142 (1999) for a description of HPTFF and conventional charged membranes), wherein the embodiment comprises use of a charged cellulose, preferably a charged composite regenerated cellulose membrane in HPTFF for the separation of a solute from a mixture of solutes, wherein the CRC membrane is prepared by actively passing reactive charged compound through the pores of the membrane. Optionally, the solute to be separated by charged membrane HPTFF is a polypeptide or protein.

These and other objects, advantages and features of the present invention will become apparent to those persons skilled in the art upon reading the details of the compositions, methods, and uses as more fully set forth below. Each reference cited herein is herein incorporated by reference in its entirety with particular attention to the description of subject matter associated with the context of the citation.

DESCRIPTION OF THE DRAWINGS

FIG. 1 is a diagram showing charged spheres representing proteins having a net charge or charge polarity based on the pKa values of amino acids at a given pH of the separation solutions (retentate and filtrate). A filtration membrane is diagrammed having a net positive charge. Flow of the separation solution is in the downward direction through the membrane, retaining proteins having the same charge polarity as the membrane (positive) in the retentate, while net neutral and negative proteins flow through the membrane with the filtrate.

FIG. 2A is a diagram of a cellulose membrane reacting with a reactive charged compound, 3-bromopropyl trimethyl ammonium bromide. The —OH moieties represent the primary alcohols of a CRC matrix. The primary alcohols react with the alkyl halide in this diagram to form a covalent ether linkage connecting the charged moiety to the cellulose matrix. FIG. 2B is a similar diagram of a cellulose membrane in which the primary alcohols reacted with a reactive charged compound, 3-bromopropyl sulfonate, to form a covalent ether linkage. In these examples, the reactions are base catalyzed.

FIG. 3 is a diagram showing a pore of a filtration membrane reacted with 3-bromopropyl trimethyl ammonium bromide. One pore is enlarged to show the charged compound linked to the surface of the pore and projecting into the lumen of the pore. As a result of the surface modification, the pore size is effectively decreased. In addition, the positive charge of the pore repels a protein of like charge, increasing the likelihood that the protein will be retained relative to neutral proteins in a mixture.

FIG. 4 is a graph showing the relationship between membrane permeability (x axis) and protein sieving (y axis) for ten commercially available uncharged filtration membranes. The graph indicates that increasing permeability corresponds to an increase in sieving. The test solutes used for the commercial membranes having a mean size of 10 kD were standardized mixed dextrans of MW 10 kD–2000 kD. "F" and "M" refer to membrane manufacturers Pall (formerly Pall-Filtron) and Millipore, respectively.

FIG. 5 is a graph showing the relationship between filtrate flux (ml/min, x axis) and sieving (y axis) for uncharged and charged membranes having 300 kD or 1000 kD MW cutoffs. Flux is proportional to membrane permeability (see, Zeman and Zydney, supra, p. 16). As flux increases, sieving increases. Unlike in conventional membranes, however, when charge is added to the membrane, the sieving coefficient of a like-charged protein decreases for a given flux value.

FIG. 6 is a graph showing the relationship between membrane permeability (y axis) and sieving (x axis) for an uncharged membrane having a 300 kD average pore size (white diamond) and an uncharged membrane having a 1000 kD average pore size (white circle) defining the solid line. A positively charged membrane having a 300 kD average pore size (black diamond) and a positively charged membrane having a 1000 kD average pore size (black circle) define the dashed line. The solute protein is positively charged recombinant human anti-HER2 monoclonal antibody (rhuMAb HER2). The data indicate that for a given permeability, sieving is dramatically decreased (in this example, by approximately two orders of magnitude) when the membrane has the same charge as the protein being tested.

Figure 7:
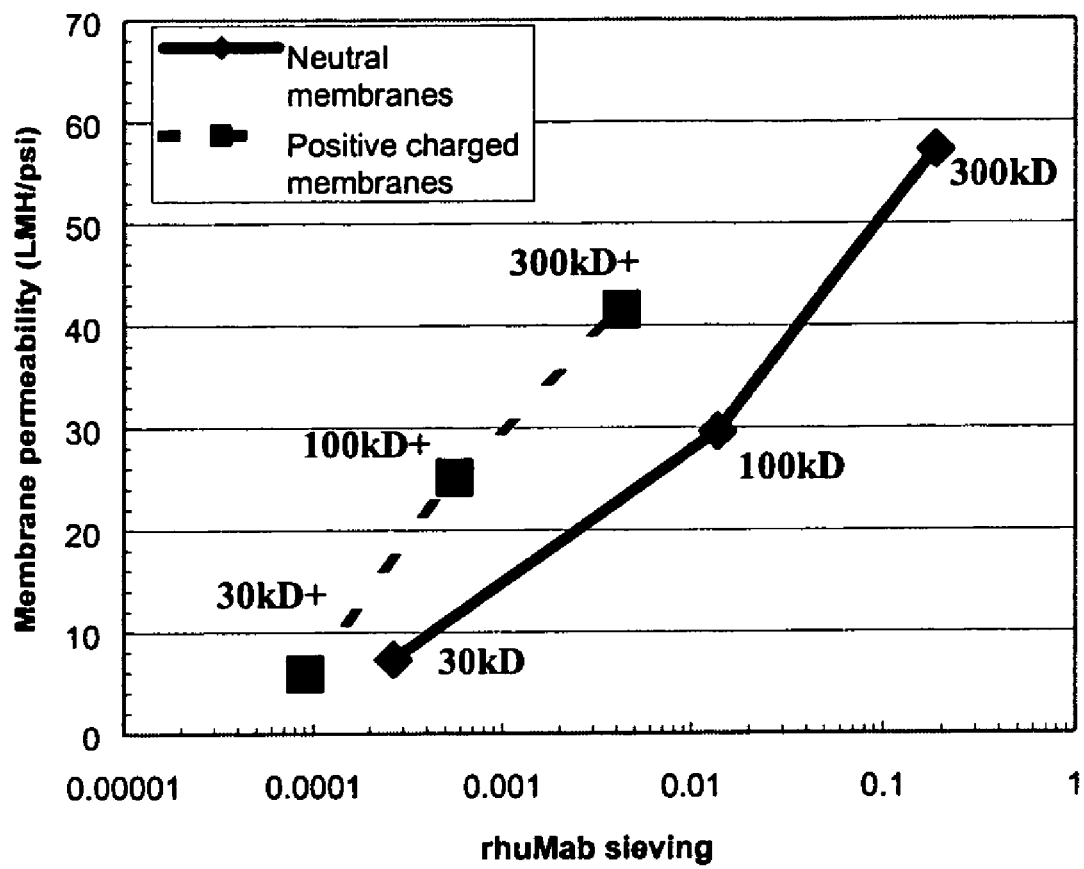
FIG. 7 is a graph of membrane sieving versus permeability for net positively charged target protein anti-CD11a rhuMab (150 kD MW) on neutral and positively charged membranes having molecular weight cut-offs (MWCO) of 30 kD to 300 kD.

Before the present filtration membranes and methods of making and using them are described, it is to be understood that this invention is not limited to the particular compositions of matter and processes described, as such compositions and methods may, of course, vary. It is also to be understood that the terminology used herein is for the purpose of describing particular embodiments only, and is not intended to be limiting since the scope of the present invention will be limited only by the appended claims.

DESCRIPTION OF THE EMBODIMENTS

Definitions

"Cellulose membrane" refers to a cellulose polymer, where the cellulose is repeating units of D-glucose, on a substrate such as a microporous membrane or non-woven substrate. Where the cellulose membrane is composite cellulose, the substrate is a microporous membrane. The hydroxyl or primary alcohol group of a glucose monomer provides the reactive species on the membrane to which the charged compound is covalently attached.

"CRC membrane" refers to a composite regenerated cellulose membrane prepared by casting cellulose on a microporous substrate to control the average pore size and limit the number of defects in the cellulose sheet. CRC membranes are preferred in the practice of the invention because they have greater mechanical strength than cellulose membranes while retaining the hydrophilicity and low fouling characteristics of cellulose useful in protein separations.

"Charged compound" refers to the compound linked to the filtration membrane, wherein the compound comprises a moiety having a positive or negative charge under the conditions used to separate a protein from a mixture of proteins. According to the invention, the charged compound may further comprise a linker arm between the membrane and the charged moiety such that the charged compound projects from the surface of the membrane. Where the charged compound projects from the surface of a pore into the lumen of the pore, the charged compound modifies the effective size of the pore and modifies the pore size distribution of the membrane.

"Reactive charged compound," "reactive compound," "reactive charged ligand," and "reactive ligand," and the like are used interchangeably herein and refer to the charged compound prior to linkage to the membrane, such that the reactive charged compound still retains the reactive moiety that promotes the membrane-reactive charged compound reaction. For example, where the charged compound is a propyl trimethyl ammonium ion covalently attached to a CRC membrane, the reactive charged compound may be bromopropyl trimethyl ammonium bromide. The covalent attachment involves nucleophilic displacement of the alkyl bromine by a primary alcohol of the cellulose matrix (see FIG. 2A, for example).

"Linker arm" refers to the portion of the charged compound molecule between the portion that reacts or has reacted with a reactive group on the surface of a filtration membrane and the charged moiety. Preferably, the linker arm is a chain of atoms or molecular subunits, which chain is inert to the reaction conditions used to covalently link the charged compound to the membrane, and is further inert to the aqueous conditions used during protein separation. A linker arm may comprise, but is not limited to, an alkyl chain of from one to twenty carbon atoms, a carbohydrate chain of from one to fifteen saccharide moities (including, for example, ribose and deoxyribose), a dextran chain of from one to fifteen saccharide moities, an amino acid chain of from one to twenty five amino acids, and other polymers (such as those used to manufacture the membrane itself) of from one to twenty five repeat units. Where a charged compound comprises an amino acid chain as a linker arm and the charged moiety is the terminal amino acid of the chain, the side chain of the terminal amino acid is preferably a charged side chain.

"Sieving" refers to the ratio of the concentration of a particular solute in the filtrate (downstream of the membrane) to the concentration of the same solute in the feed solution (upsteam of the membrane) (see Zeman and Zydney, supra, p. 308). Generally a high sieving value suggests that the solute readily passes through the membrane, while a low sieving value suggests that the solute is largely retained by the membrane. Where it is desired to retain a solute upstream of the membrane and the charge polarity of the solute and charged membrane are the same, a reduced sieving coefficient is preferred.

"Permeability" refers to the filtration rate divided by the net pressure drop across the membrane. Permeability is therefore the inverse of membrane resistance. Membrane permeability is primarily determined by pore size distribution, porosity (pore density), membrane thickness, and solvent viscosity. For an uncharged membrane, permeability generally decreases as sieving decreases. According to the invention, the addition of a charged compound to the membrane results in an improvement in sieving improvement relative to an uncharged membrane or population membranes of the same type. Further according to the invention, the sieving improvement is accompanied by substantially no change in permeability, or alternatively, the change in permeability is of a lower magnitude than the change in sieving such that the combination of the sieving and permeability characteristics are improved relative to a membrane lacking the charged compound. These improvements are illustrated by a graph in which sieving and permeability are plotted and, following covalent attachment of a charged compound, the plot shifts to improved sieving values. Where the solute of interest is of the same charge polarity as the charged membrane, the improvement is observed as reduced sieving accompanied by a smaller reduction or no reduction in permeability. According to the invention, the improvement in sieving is by at least 1.5 fold, alternatively at least 5 fold, at least 10 fold, at least 20 fold, at least 50 fold, or at least 100 fold lower relative to the sieving value of an uncharged membrane (see, for example, FIGS. 6–11). By the phrases "no reduction in permeability" or "the same permeability" is meant a permeability of a charged membrane that is within 50%, preferably 30%, more preferably within 10% of the permeability of an uncharged membrane of the same type. Thus, where the improvement is a reduction in sieving because a charged solute, such as a protein, is retained by a like-charged membrane, the sieving is a reduction at comparable or substantially the same permeability, or a permeability that is reduced less than the sieving is reduced. Consequently, the rate of filtration is largely maintained, while the selectivity of the membrane is improved.

"Net charge" when referring to a membrane or protein charge is meant a charge polarity that is predominately positive or negative, but does not refer to a specific value for the number of positive charges versus the number of negative charges on the membrane or protein, unless otherwise noted. Similarly, "like charge" and "same charge" refer to the situation in which a protein having a given charge polarity, positive or negative, is related to a membrane or other protein having a given charge polarity, either positive or negative.

"Protein mixture" refers to various proteins of different sizes and net charges under given separation conditions of pH and ionic strength. According to the separation method of the invention, when the net charge of a protein of interest is known or is manipulated by alteration of pH conditions to have a net positive charge or net negative charge, the protein may be separated from differently charged or neutral proteins by passing the protein mixture through a membrane of the invention having the same charge polarity as the protein of interest (i.e., either a net positive charge or a net negative charge). For example, the invention contemplates a method of separating a desired protein from at least one protein of a mixture of proteins in an aqueous buffered solution, altering the pH of the solution such that the desired protein has a net charge and a protein to be separated from it is neutral or has a net charge that is opposite the net charge of the desired protein. Next the protein mixture is contacted with a charged cellulose filtration membrane of the invention wherein the desired protein and the membrane have like net charges. The desired protein is separated from the neutral protein and the oppositely charged protein by retaining the desired protein upstream of the membrane and filtering the neutral or oppositely charged protein through the membrane. This process is repeated until the desired protein is separated from a chosen number of proteins of the mixture.

Alternatively, the invention contemplates a method of separating a desired protein from at least one protein of a mixture of proteins in an aqueous buffered solution by altering the pH of the solution such that the desired protein is neutral and the protein to be separated from it has a net charge that is the same as the charged membrane. Next the protein mixture is contacted with the charged cellulose filtration membrane of the invention. The desired protein is separated from the charged protein by retaining the charged protein upstream of the membrane and filtering the desired protein through the membrane. This process is repeated until the desired protein is separated from a chosen number of proteins of the mixture.

"Pore size distribution" refers, basically, to the number of pores having an actual radius, R, near some theoretical radius, r, expressed as the probability density function (see, Zeman, L. J. and Zydney, A. L., supra, p. 299–301). As the standard deviation of actual pore radii increases, the pore size distribution increases. Narrowed pore size distribution results from a reduction in the standard deviation of the pores from the theoretical value. This is achieved, for example, when the sizes of some of the larger pores are reduced by addition of charged compound into the larger pores of a charged membrane. FIG. 3 diagrams such a pore size reduction. The principle of liquid-liquid pore intrusion is useful for measuring pore size distribution (see R. van Reis and A. L. Zydney, supra, p. 2201). According to this principle, two highly immiscible liquids, such as solutions of a sulfate salt and a poly(ethylene glycol) are contacted through mixing to reach equilibrium partitioning. The membrane to be tested is primed with one of the liquids so that all pores are filled. After draining the feed channels, the second fluid is introduced into the system. The first fluid is then displaced out of the pores by the second fluid, and the flow rate is measured as a function of trans-membrane pressure. The resulting data provide information on pore size distribution and can be correlated with the nominal molecular weight cutoff (see R. van Reis and A. L. Zydney, supra, p. 2201).

The term "active flow" as used herein refers to a net flow of solvent and/or charged reactive ligand through pores of a porous filtration or chromatography medium, such as a porous resin or membrane. Typically, flow is from one exterior surface of the porous medium, through a pore within the medium, and out of a pore at another exterior surface. Where the porous medium is a filtration membrane, the membrane typically has a macroscopically flat appearance, a first (retentate) surface, a second (filtrate) surface, and pores for fluid flow between the retentate and filtrate surfaces of the membrane, where the pore surfaces constitute a third collective surface. A net flow of solvent and/or reactive charged ligand from the retentate side (upstream) to the filtrate side (downstream) of the membrane and is typically caused by a pressure differential between different exterior surfaces of a porous medium. Where the porous medium is a membrane, a pressure differential is between the retentate side and filtrate sides of the membrane. The pressure differential may be generated by any suitable means, such as by a pump creating lower pressure on the filtrate side, a pump creating higher pressure on the retentate side, gravity, centrifugal force, and the like. Typically, solvent flow will be normal (perpendicular) to the membrane, although solvent flow tangential to the membrane (tangential flow or cross flow) will also result in a net solvent and/or charged reactive ligand flow through membrane pores when a sufficient pressure differential between the retentate and filtrate sides exists. Sufficient pressure differential is that difference in pressure between the retentate and filtrate sides of a membrane that causes solvent and/or charged reactive ligand to pass through pores of the membrane such that a net flow occurs primarily in one direction (typically from the retentate to the filtrate side of a membrane), or the net flow may be by Starling Flow. Active flow through a membrane causes solvent to pass through pores of the membrane carrying charged reactive ligand capable of entering the pores. Where the reactive ligand compound is capable of reacting with functionalities on the surface of the membrane, membrane and pore surfaces become derivatized such that the surfaces have a net charge of the sign of the charged reactive ligand. According to the present invention, a membrane is derivatized by contacting the membrane with a reactive ligand compound capable of reacting with a functionality on the membrane surface. Where such contacting is by active flow, a membrane surface and pore surface are derivatized by contacting a solvent and solute with the membrane and causing them to pass through a membrane pore. The reactive solute reacts with and becomes covalently bound to the membrane surface and pore surface. Where the reactive ligand compound comprises a charged moiety, the membrane surface and pore surface gain a net charge. According to the method of the invention, active flow may comprise recirculation of solvent and solute such that they contact the membrane surface, including the pore surface, repeatedly so as to ensure adequate derivatization.

The term "no flow" as used herein refers to the absence of a net flow of solvent and/or charged reactive ligand through pores of a-porous filtration or chromatography medium, such as a resin or membrane. Under conditions of no flow, there is an absence of a sufficient pressure differential between exterior surfaces of the porous medium to cause a net flow of the solvent and/or charged reactive ligand through pores of the porous medium. Where the medium is a membrane exposed to conditions of no flow, there is insufficient pressure differential between the retentate and filtrate sides of a membrane to cause net flow through membrane pores. Insufficient pressure differential is that difference in pressure between the retentate and filtrate sides of a membrane that is too low to cause solvent and/or charged reactive ligand to pass through pores of the membrane such that a net flow fails to occur. Under no flow conditions, solvent and solute may contact all surfaces of the membrane, such as by emersion of the membrane in solvent containing a solute, but due to lack of a net flow through the pores, the solvent and/or charged reactive ligand fail to contact pore surfaces because surface tension at the pore opening, electrostatic repulsion at the pore as derivatization of the exterior membrane surface progresses, or other passive phenomena prevent solvent and/or charged reactive ligand to enter the pores. Where the solute is a reactive ligand compound capable of reacting with functionalities on the surface of the pore, the membrane surface, but not the pore surfaces, becomes derivatized by the charged reactive ligand under no flow conditions. Where the reactive ligand compound comprises a charged moiety, the membrane surface, but not the pore surfaces, gains a net charge under no flow conditions.

EXAMPLES

The following examples are provided so as to provide those of ordinary skill in the art with a complete disclosure and description of how to make the compositions of the invention and how to practice the methods of the invention and are not intended to limit the scope of what the inventor regards as his invention. Efforts have been made to insure accuracy with respect to numbers used (e.g. amounts, temperature, etc.), but some experimental errors and deviation should be accounted for. Unless indicated otherwise, temperature is in degrees C., chemical reactions were performed at atmospheric pressure or transmembrane pressure, as indicated, the term "ambient temperature" refers to approximately 25° C. and "ambient pressure" refers to atmospheric pressure.

Example 1

Adding Charge to Membrane Using Active Flow and no Flow Processes

Frequently, filtration membrane material, such as composite regenerated cellulose membranes, are available in bulk as flat sheets. The present example discloses how the invention may be used to add charge to membrane sheets using the active flow method of the invention. It is understood that the same or similar method is useful for adding charge to a pre-packaged uncharged membrane in its membrane cartridge, an alternative form in which many membranes are commercially available.

The experimental conditions are the following. Composite regenerated cellulose membranes (Millipore, Bedford, Mass.) with a nominal molecular weight cut-off of a) 100,000 and b) 300,000 Daltons are used for the present example. The membranes are provided in the form of flat sheet disks. Each disk is assembled in a device suitable for contacting solvent and reactive ligand with the membrane and optionally capable of causing solvent and/or ligand to pass through membrane pores from the retentate (upstream) side of the membrane to the filtrate (downstream) side. See, for example, Amicon® Stirred Ultrafiltration Cells (Millipore, Bedford, Mass.) as devices useful for this purpose. The device may also have the capability of recirculating solvent and reactive ligand from the filtrate to the retentate side of the membrane. Each membrane disk is placed on top of a non-woven substrate of the same size to prevent membrane occlusion from the membrane holder filter support. Each membrane is flushed with 70/30 volume/volume (v/v) isopropyl alcohol solution (IPA) in deionized distilled water followed by further flushing with deionized distilled water to remove any wetting agents, where flushing includes rinsing the surface of the membrane with each solution as well as drawing each solution through the membrane pores. Useful solvent fluxes for reacting a charged reactive compound with a membrane according to the invention is a solvent flux that allows a given reactant sufficient time in contact with the surface to react with it. Such a useful flux is at least 1 LMH (liters per square meter per hour), alternatively at least 10 LMH, at least 50 LMH, at least 100 LMH, at least 200 LMH, or at least 300 LMH. The transmembrane pressure drop across the membrane is adjusted by nitrogen pressurization and/or by controlling the filtrate flux after connecting a peristaltic pump to the filtrate line. A pressure drop useful for the invention is a function of the pore size and is readily determined for particular conditions of the reaction. The stirring speed is adjusted using a magnetic stirrer with the actual speed evaluated using a tachometer. The magnetic stirrer may be suspended above the membrane to prevent damage to it during stirring. The membrane is then flushed with a 0.1N NaOH aqueous solution by rinsing the membrane surface and passing the 0.1N NaOH solution through the membrane pores under pressure.

A non-limiting list of reactive ligand compounds useful for adding charge to a porous filtration medium, including but not limited to a filtration membrane, is provided in Table 1. The list includes reactive ligand compounds that can impart a charge to the membrane when covalently bound to it. Reactive ligand compounds imparting a positive or negative charge are listed. Also included in the list are a non-limiting selection of reactive compounds that can act as linker compounds. These molecules possess a halide moiety capable of reacting with the membrane (and pore) surfaces as well as a hydroxyl moiety capable of reacting with a second reactive ligand compound that imparts charge to the membrane.

TABLE 1

Reactive Ligand Compounds*

Positively charged ligands (2-bromoethyl)trimethylammonium bromide
(3-bromopropyl)trimethylammonium bromide
(3-bromopropyl)triethylammonium bromide
(3-carboxypropyl)trimethylammonium chloride
(3-chloro-2-hydroxypropyl)trimethylammonium chloride
(5-bromopentyl)trimethylammonium bromide
(2-chloroethyl)trimethylammonium chloride
(2,3-epoxypropyl)trimethylammonium chloride
2-(diethylamino)ethyl chloride hydrochloride
2-chloroethylamine monohydrochloride
3-chloropropylamine hydrochloride
1-chloro-2-dimethylaminoethane hydrochloride
2-chloro-1-dimethylaminopropane hydrochloride
2-bromoethylamine hydrobromide Negatively charged ligands 3-bromopropanesulfonic acid sodium salt
2-bromoethanesulfonic acid sodium salt
3-chloro-2-hydroxy-1-propanesulfonic acid sodium salt hydrate
3-chloroethanesulfonic acid sodium salt monohydrate
chloroacetic acid sodium salt
3-chloropropionic acid
2-bromo-2-methyl-propionic acid
3-bromo-2-methylpropionic acid
bromoacetic acid
3-bromopropionic acid
4-chlorobutyric acid
4-bromobutyric acid
6-bromohexanoic acid
8-bromooctanoic acid
11-bromoundecanoic acid
2-bromohexanedecanoic acid
15-bromopentadecanoic acid
16-bromohexanedecanoic acid
12-bromododecanoic acid
3-chloro-2,2-dimethylpropionic acid
bromomethanesulfonic acid sodium salt Linker Ligands 12-bromododecanol
2-bromoethanol
3-bromo-1,2-propanediol
3-bromo-1-propanol
6-chlorohexanol
3-chloro-1,2-propanediol
3-chloropropanol
11-bromo-1-undecanol

*The list of ligands in Table 1 is a non-limiting list of compounds useful in the invention.

After reacting the membrane with a charged ligand, the membrane hydraulic permeability, Lp=J/P, in 0.1N NaOH solution is measured. This measurement is performed by determining the slope of a curve describing the filtrate flux (J) as a function of pressure (P) using at least three data points. As shown, below, the permeability of a membrane is a performance characteristic useful for comparing membranes of different MWCOs and/or charge.

Adding Charge to a Membrane Using the Active
Flow Method (Active Flow Mode)

The stirred cell is filled with 0.1N NaOH solution and passed through the membrane at a filtrate flux of 100 LMH (liters per square meter per hour). The stirred cell is filled with the reactant solution comprising a solvent and a reactive ligand, where the ligand is a reactant capable of covalently binding to funtionalities on the membrane surface and pore surfaces and, once bound, capable of forming a charge on the membrane. Alternatively, where the bound reactant is a linker molecule, it may be derivatized with a second reactant that creates the charge. Typically, the reactant solution is stirred in the retentate chamber, passed through the membrane pores into a filtrate chamber, and recirculated back to the retentate chamber using a peristaltic pump at a filtrate flow rate of 50–100 LMH. Typically, the reaction is performed for 16 hours or overnight at ambient temperature, although the temperature and duration may be adjusted as appropriate for the specific reaction conditions to achieve complete reaction. After the reaction is complete, the reactant solution is discarded from the stirred cell and the membrane is flushed with distilled deionized water followed by 1% v/v acetic acid/0.12 M phosphoric acid to quench the reaction. The membrane is then flushed by rinsing the membrane surface with distilled deionized water and passing distilled deionized water through the membrane pores. Membrane permeability in 0.1N NaOH is measured as described above, herein. The membrane will then either be used for a Flex Test or stored in 0.1N NaOH until use.

Adding Charge to the Membrane in the Absence of Active Flow (No Flow Mode)

The membrane disk is prepared as described above, except that the stirred cell is used at ambient pressure and fluids are not observed to flow through the membrane pores during the reaction. After the 0.1N NaOH solution is flushed through the membrane, the reactant solution is added. The reaction of reactant with the accessible membrane surfaces is allowed to continue for 16 hours or overnight. The reactant solution is discarded and the membrane is rinsed at ambient temperature and pressure with distilled deionized water. No fluid flow through the membrane pores is observed during rinsing at ambient pressure. The membrane is then rinsed with 1% v/v acetic acid/0.12 M phosphoric acid and the solution is passed through the membrane pores to quench the reaction on the exterior membrane surface and pore surfaces. The membrane is then rinsed by passing distilled deionized water over the membrane surface and through the membrane pores. The membrane permeability in 0.1N NaOH is determined as described above. The membrane is then stored in 0.1N NaOH at ambient temperature.

Flex Test for Evaluating Membrane Permeability and Sieving Properties

The permeability and sieving properties of membranes before and/or after reaction with a reactant may be evaluated by determining the relative retention of a charged or neutral molecule by a membrane as solvent is passed through it under controlled conditions. The Flex Test is useful for that purpose. See, for example, Gabriel Tkacik and Stephen Michaels (Biotechnology 9:941–946 (1991) in which the authors describe test for measuring solute rejection (R) by neutral ultrafiltration membranes, herein incorporated by reference in its entirety. The Flex Test described herein furthers measurement by plotting solute sieving (S) (where S is related to rejection by the function: R=1−S) on a log scale for better accuracy, by using fluorescently tagged dextrans for improved detection sensitivity at low sieving, and by applying the analysis to both neutral and charged membranes. Briefly, the Flex Test consists of first adding a solution of polydisperse dextrans to the retentate side of a membrane in a stirred cell, passing the solution through the membrane at positive pressure to the filtrate side and recirculating the solution back to the retentate side for approximately 30 minutes at ambient temperature to allow the system to equilibrate. When equilibrium is achieved, retentate and filtrate samples are taken to evaluate the dextran retention for each different dextran molecular weight (MW) for positively charged and neutral dextrans.

The charged dextrans used are fluorescently tagged to enhance assay sensitivity thus allowing for accurate determination of lower sieving values. For example, the fluorescent positively charged dextrans were prepared from neutral dextrans that were reacted with diethylaminoethyl chloride to give positively charged diethylaminoethyl dextrans (DEAE-dextrans). The DEAE-dextrans were then reacted with tetramethyl rhodamine B isothiocyanate (TRITC) to give the positively charged TRITC-DEAE-dextrans. Charged dextrans were obtained from TdB Consultancy AB, Uppsala, Sweden.

A mixture of positively charged dextran solutions for testing (mixture of "positive test dextrans") were prepared by suspending positive test dextrans of three molecular weights (MW) (10, 110 and 800 kD) in 10 mM Bis Tris buffer (pH=6.5). The final dextran concentration in the solution was 10 mg/ml while the ratio of 10 kD:110 kD:800 kD positive test dextrans in the solution was 3:2:5.

For example, to test positively charged membranes, permeability is measured in 0.1N NaOH as described herein, above, where permeability is Lp=J/P. Following a permeability determination, the Flex Test is performed on a membrane as follows. Each membrane to be tested (net positively charged membranes prepared under active flow versus no flow conditions, or net negative membranes prepared under active flow versus no flow conditions) is placed in a stirred cell and equilibrated with 10 mM Bis Tris buffer (pH=6.5) by passing the buffer through the membrane. The buffer is then discarded and the membrane is tested with positively charged and neutral (uncharged) dextrans to determine sieving characteristics of the positively charged membrane. For example, a useful positively charged dextran is TRITC-DEAE dextran (TdB Consultancy AB, Uppsala, Sweden). The dextrans are introduced onto the retentate side of the membrane. The stirring speed is adjusted to ensure optimum mass transfer characteristics. For example, the filtrate rate is set to 10 LMH using a filtrate pump to minimize membrane fouling and/or concentration polarization. A recirculation time of approximately 15–30 minutes, preferably about 30 minutes, at ambient temperature is used to allow for system equilibration. Filtrate and retentate samples are collected at the end of the 30 minute recirculation period. The TRITC-DEAE solution is then discarded and the membrane is rinsed with 0.1N NaOH by rinsing the membrane and passing the NaOH solution through the membrane pores.

The same membrane is retested using neutral test dextrans (available from TdB Consultancy AB, Uppsala, Sweden). The membrane is re-equilibrated with 10 mM Bis Tris buffer by passing the buffer through the membrane. After 30 minutes of recirculation a new set of filtrate and retentate samples is collected.

A similar series of tests are performed for negatively charged membranes prepared by active flow and no flow conditions, where the dextrans used are negatively charged and neutral.

Collected samples are assayed using an HP1100 high performance liquid chromatography (HPLC) system (Hewlett Packard, Palo Alto, Calif.) and a Shodex OHPak 806M HQ size exclusion chromatography column (Shodex, Japan) with 10 mM Bis Tris/10% v/v of 5M NaCl at pH 6.5 as a running buffer at a flow rate of 0.5 ml/min. A refractive index detector and a fluorescence detector (for TRITC, excitation: 245 nm, emission: 572 nm) are used to analyze the samples. For each sample pair (filtrate and retentate samples for a particular membrane being tested), signal intensity is plotted versus dextran molecular weight.

A graph in which sieving values are plotted versus dextran molecular weight curve for each membrane is prepared. The sieving values are determined by calculating the ratio of the filtrate sample signal intensity divided by the retentate sample signal intensity for each dextran and plotting that ratio (the sieving value) against the molecular weight of the dextran. From the dextran sieving curves, the selectivity at a sieving ratio of 100 is determined as follows. The molecular weight value for an uncharged dextran having a sieving value of 0.1 is read from the curve is divided by the molecular weight of a charged dextran (either positive or negative) having a sieving value of 0.001 which is also read from the curve. This molecular weight ratio is a standard measure of the ability of a given membrane to separate solutes, such as products and impurities, for each membrane prepared.

The sieving versus permeability plots described herein are an alternative measure of membrane performance regarding membrane flow and retention characteristics. A shift in the plot toward lower sieving values is typically seen for charged membranes relative to uncharged membranes. This indicates that a charged membrane prepared according to the active flow method disclosed herein has improved sieving (greater retention of solutes having a net charge of the same sign as the charged membrane and less retention of net neutral solutes) relative to an uncharged membrane.

Using the methods disclosed herein, adding charge to a filtration membrane, such as a CRC membrane, improves sieving at least 1.5 fold, alternatively at least 5 fold, at least 10 fold, at least 20 fold, at least 50 fold, or at least 100 fold relative to the sieving value of an uncharged membrane, and/or a plot of sieving versus permeability shifts toward improved sieving values (see, for example, FIGS. 6–11). Where the solute to be separated is of the same charge polarity as the charged membrane, the improvement is to a lower sieving value. Where the solute to be separated is of the opposite polarity as the charged membrane, the improvement is to a higher sieving value.

In the present example, membrane sheets are cut into disks and derivatized in a stirred chamber. For larger disks or large sheets, incorporation of the membrane into a chamber of sufficient size to contain the membrane, create a pressure differential between the retentate and filtrate sides of the membrane or otherwise allow flow through membrane pores (such as by active flow with optional recirculation of reactive ligand) can be performed based on the disclosure provided herein. In addition, uncharged membranes prepackaged in cassette cartridges may be derivatized in the cartridge as described in Example 6, herein.

Example 2

Preparation of Charged CRC Filtration Membranes

For illustrative purposes, this example discloses charged CRC membranes and methods of making them. It is understood that charge may be added to a membrane by chemistries known to one of ordinary skill in the art such that the product membrane is charged and selectively retains a desired protein in the retentate, and passes uncharged or oppositely charged proteins with the filtrate. The product charged membrane has the characteristic of a lower sieving coefficient for a given permeability relative to an uncharged membrane, or a higher permeability for a given sieving coefficient.

CRC membranes are preferred due to their hydrophilicity as well as their mechanical stability to reverse pressure. Stability under basic conditions allows for complete, rapid cleaning and storage. CRC membrane hydrophilicity minimizes protein fouling and simplifies membrane cleaning. The membranes are preferably reacted with the reactive charged compound in an aqueous solution. Aqueous reaction conditions are advantageous because flammable, organic compounds are avoided and the aqueous-soluble compounds are more readily and completely removed from a charged CRC membrane intended for use in pharmaceutical applications. CRC membranes were obtained from Millipore, Corp. (Bedford, Mass. The 300 kD MW membranes were designated PLCMK. The 1000 kD MW membranes were designated PLCXK).

The primary alcohol or hydroxyl groups of the D-glucose moieties of cellulose are targeted for derivatization because they can react without undermining the integrity of the cellulose matrix. Primary alcohols (R—OH) react with alkyl halides (R'—X, where X is Br, for example) to produce ethers (R—O—R'). In this example, a CRC membrane was reacted with 2 molar 3-bromopropyl trimethyl ammonium bromide (as diagrammed in FIG. 2A) in 0.1 N NaOH at room temperature overnight. The reacted membranes were washed in distilled water and used for protein filtration or stored in 0.1 N NaOH at ambient temperature. The membranes are stable at these conditions for at least twelve months.

The quaternary ammonium ion has a positive charge in aqueous solution from approximately pH 2 to pH 10, inclusive. This pH range corresponds to the pH range in which most proteins are structurally intact or recoverable to an active state, making a quaternary amine useful as the charged moiety of the charged compound. Halides such as bromide, chloride, and iodide are useful reactive moieties because they are good leaving groups for nucleophilic attack by the oxygen of the primary alcohol. It is understood, however, that other anionic groups well known to those of ordinary skill in the art may be used to facilitate the reaction.

Reacting the alkyl halide directly with a hydroxyl moiety or primary alcohol of the cellulose is advantageous because it is a one-step reaction. This method also has the advantage of avoiding the need to first derivatize the membrane with a strongly nucleophilic moiety that may not be fully reacted during subsequent steps or may require additional reactions to remove or deactivate the added nucleophile. Another advantage of the method is that many alkyl halides are commercially available (see Table 1). Thus, the method of preparing the charged membranes of the invention is rapid and convenient, thereby saving time and cost.

Negatively charged membranes were generated using a similar method. The reactive ligand compound was 2 molar 3-bromopropane sulfonic acid in 0.1 N NaOH. The reaction is diagrammed in FIG. 2B, and the reaction conditions were as disclosed above for 3-bromopropyl trimethyl ammonium bromide. The sulfonic acid moiety remains negatively charged in a pH range useful for many protein separations.

To verify that a positively or negatively charged CRC membrane was uniformly derivatized, the membranes were stained with a dye having a charge opposite that of the tested membrane. CRC-O-propyl trimethyl ammonium bromide membranes were rinsed extensively in distilled water and dipped in aqueous ponceau red solution. The negatively charged dye uniformly stained the positively charged membrane, but did not stain a control membrane that had been exposed to 0.1 N NaOH without the 3-bromopropyl trimethyl ammonium bromide. Similarly, CRC-O-propane sulfonic acid membranes were extensively rinsed in distilled water and dipped in aqueous methylene blue solution. The positively charged dye stained the negatively charged membrane, but did not stain the control membrane that had been exposed to 0.1 N NaOH in the absence of 3-bromopropane sulfonic acid. Thus, the membranes were uniformly and extensively derivatized by the alkyl halides in this example.

Example 3

Membrane Pore Size Distribution is Modified

Membrane pores are infiltrated by reactive charged compounds under positive pressure when steric factors, such as size and linker arm length, and electrostatic factors, such as charge repulsion, allow it. Thus, according to the invention, membrane pores large enough to allow infiltration of a given reactive charged compound are derivatized by the charged compound such that the size of the pore lumen is reduced. FIG. 3 shows a diagram of a membrane pore having propyl trimethyl ammonium ions covalently attached to the wall of the pore and projecting into the lumen.

The length of the linker arm controls the degree to which the charged compound projects into the lumen and reduces its effective diameter. The charge generates a positively charged region from which a similarly charged protein will be excluded. Thus, a desired protein having an overall charge that is the same as that of the derivatized membrane is repelled by the surface of the membrane as well as by the pores of the membrane, thereby improving retention of the desired protein. Neutral proteins will tend to pass through the charged membrane pores with the filtrate, being neither attracted to nor repelled from the surface or pores of the membrane.

Example 4

Methods of Using a Charged CRC Membrane to Separate Proteins

Using conventional membranes, permeability is sacrificed for improved sieving, or sieving is sacrificed for improved permeability. In general, as permeability of a membrane increases, the sieving coefficient increases. This reflects the fact that more of the protein to be retained passes through a highly permeable membrane, making the filtration process faster, but less selective (high sieving coefficient), resulting in lower yield of desired protein and less complete separation. FIG. 4 is a graph demonstrating that commercial ultrafiltration (UF) membranes sacrificed sieving for improved permabililty. The UF membranes of FIG. 4 were tested using a standardized mixed dextran test (see, for example, Zeman and Zydney, supra, p. 183–88). The tested membranes were from Pall Filtron (Cellulose, Omega™ (polysulfone with hydrophilic modification), Alpha™ (polyethersulfone modified to lower fouling), and Nova™ (polyethersulfone)) and Millipore (Regenerated Cellulose (RC), Biomax™ with screen A, Biomax™ with screen B, and PES (polyethersulfone)). The performance of Biomax™ polyethersulfone membranes in HPTFF for protein separation was reported by R. van Reis et al., J. Memb. Sci. 159: 133–142 (1999).

The charged membranes of the invention decrease the sieving coefficient for a given permeability when compared to an uncharged membrane. By charge-modifying an uncharged membrane, the problem of sacrificing sieving for permeability (or vice versa) is solved. The membranes of the invention have dramatically improved sieving for a given permeability when compared to the uncharged control membrane.

FIG. 5 shows the relationship between filtrate flux (ml/min, x axis) and sieving (y axis) for uncharged and charged membranes having 300 kD or 1000 kD MW cutoffs. As flux, a factor that is proportional to membrane permeability (see, Zeman and Zydney, supra, p. 16), increases, sieving increases. Unlike in conventional membranes, however, when charge is added, the sieving coefficient decreases for a given flux value. At a relatively high flux of 8 mL/min (see "a" on FIG. 5), a 1000 kD CRC charged membrane (CRC 1000+) or a 300 kD CRC charged membrane (CRC 300+) has an approximately 10 fold lower sieving coefficient than the uncharged control membrane. At a lower flux of 5 mL/min (see "b" on FIG. 5), the sieving coefficient is reduced approximately 100 fold for both the 1000 kD and the 300 kD CRC charged membranes. In this example, the charged compound added onto the surface and into the pores of the CRC membrane was propyl trimethyl ammonium ion. The membranes were prepared as disclosed in Example 1. The protein was rhuMAb HER2 under conditions that rendered it positively charged, like the CRC+ membrane. The sieving coefficient was calculated using the rhuMAb HER2 concentration (ng/mL) in the filtrate (determined by ELISA) divided by the rhuMAb HER2 concentration in the feed solution (known).

The data at point "b" of FIG. 5 were recalculated and plotted to show the relationship between permeability and sieving in FIG. 6. These data also show that for a given permeability, the sieving is reduced 100 fold for both 300 kD and 1000 kD MW cutoff CRC membranes when charge is added. Thus, an optimum permeability may be chosen to allow rapid separation, while greatly improving (rather than harming) the sieving coefficient for the membrane and allowing improved separation and yield of the desired protein. These dramatic and unexpected improvements in membrane properties result from the addition of charged compounds to the surface and pores of the membrane.

Separation of a mixture of proteins according to the invention. A mixture of proteins, each having a different pI were separated using the charged membranes of the invention. In a first example, two proteins were separated. RhuMAb HER2, the desired protein, has pI 8.9. Bovine serum albumin (BSA), an impurity, has pI 4.8. The proteins were mixed in a pH 4.5 buffer causing rhuMAb HER2 to be highly positively charged, and BSA to be neutral or with a very slight positive charge. A positively charged membrane of the invention, such as a CRC-O-propyl trimethyl ammonium membrane was used for the separation. The proteins and buffer were contacted with the positively charged membrane. Of the two proteins, only BSA passed through the membrane into the filtrate because it was not repelled by the positive surface or pores of the membrane. The desired protein, rhuMAb HER2 was retained upstream of the positively charged membrane.

A related strategy is useful for retaining a protein, such as BSA in this example, which has pI 4.8, while the desired product protein, for example, rhuFab (e.g. anti-VEGF Fab), having a pI of 8.1, is allowed to pass through a membrane to effect separation of the two similarly sized proteins, in this example 68 kD and 45 kD, respectively. The separation is performed using a pH 8 buffer, thereby causing rhuFab to be net neutral. The BSA and Fab protein mixture in pH 8 buffer is contacted with a CRC-O-propane sulfonic acid membrane of the invention (negatively charged at pH 8) to allow the higher pI protein (Fab, pI 8.1) to pass through the membrane into the filtrate and retain the lower pI, negatively charged protein (BSA, pI 4.8) upstream of the negatively charged membrane.

A pH gradient may be preferred over the step-wise pH change described above, although a similar strategy for selective protein retention and removal is followed.

Example 5

Sieving Properties of Charged Membranes Prepared by the Active Flow Process

Using selected proteins, sieving properties of charged composite regenerated cellulose membranes having charge on the exterior and pore surfaces (e.g., prepared by the method described in Example 1, herein) were tested. For the preparation of positively charged membranes, neutral CRC membranes (Millipore, Bedford, Mass.) were reacted with (3-bromopropyl) trimethylammonium bromide. For the preparation of negatively charged membranes, neutral CRC membranes were reacted with 3-bromopropanesulfonic acid sodium. The experimental conditions for the various sieving experiments were as follows. The five target protein pharmaceuticals included a recombinant human monoclonal antibody (rhuMab anti-CD11a), two antibody fragments (rhuFab (anti-VEGF Fab) and rhuF(ab')$_2$ (anti-CD18)) and two smaller protein molecules, recombinant human growth hormone (rhGH) and DNase. Experiments were performed with recirculation of protein mixture by returning both retentate and filtrate to the feed tank at least once during the purification and collecting filtrate and retentate samples. Recirculation was performed until equilibration for each flux point. Protein concentration in the retentate and filtrate was measured by UV measurements, HPLC and ELISA assays. Sieving was calculated as the ratio of the target protein concentration in the filtrate over the target protein concentration in the retentate. Sieving was evaluated for positively charged target proteins on neutral and positively charged membranes, as well as for negatively charged target proteins on neutral and negatively charged membranes. In addition, sieving of the target proteins was determined for at least three neutral membranes having different molecular weight cut-offs (MWCO), where MWCO is a function of the membrane pore size. These results were compared to retention on the same MWCO membranes after charge was added to the membrane exterior and pore surfaces as described in Example 1, herein.

In general, the charged membranes exhibited lower target protein sieving (increased retention by the membrane) compared to uncharged membranes by at least 1.5 fold, alternatively at least 5 fold, at least 10 fold, at least 20 fold, at least 50 fold, or at least 100 fold relative to the sieving value of an uncharged membrane, where the permeability is substantially the same or where the sieving versus permeability curve shifts toward lower sieving values. This finding is shown in the Figures, particularly FIG. 6, as described in Example 4 herein, and in FIGS. 7–11, as described below.

FIG. 7 is a graph of the sieving values versus permeability for a positively charged human recombinant monoclonal antibody (rhuMab anti-CD11a, MW 150 kD, Genentech, Inc.)) on neutral and positively charged membranes of nominal MWCOs 30, 100 and 300 kD. Sieving data are presented as a function of membrane permeability measured in water. The isoelectric point of the target protein in FIG. 7 is 9.3. During purification, the buffer conditions were maintained at an ionic strength <1 mS/cm and a pH of 6, causing the target protein to have a net positive charge during the purification. By applying a positive charge to the exterior and pore surfaces of the membrane, a significant decrease in sieving (increased retention) was achieved for all of the positively charged membranes having various molecular weight cut-offs (different average pore sizes). The sieving on the positive charged 100 kD membrane is 10-fold less than the sieving on the neutral 100 kD membrane although the two membrane permeabilities are substantially the same.

Figure 8:
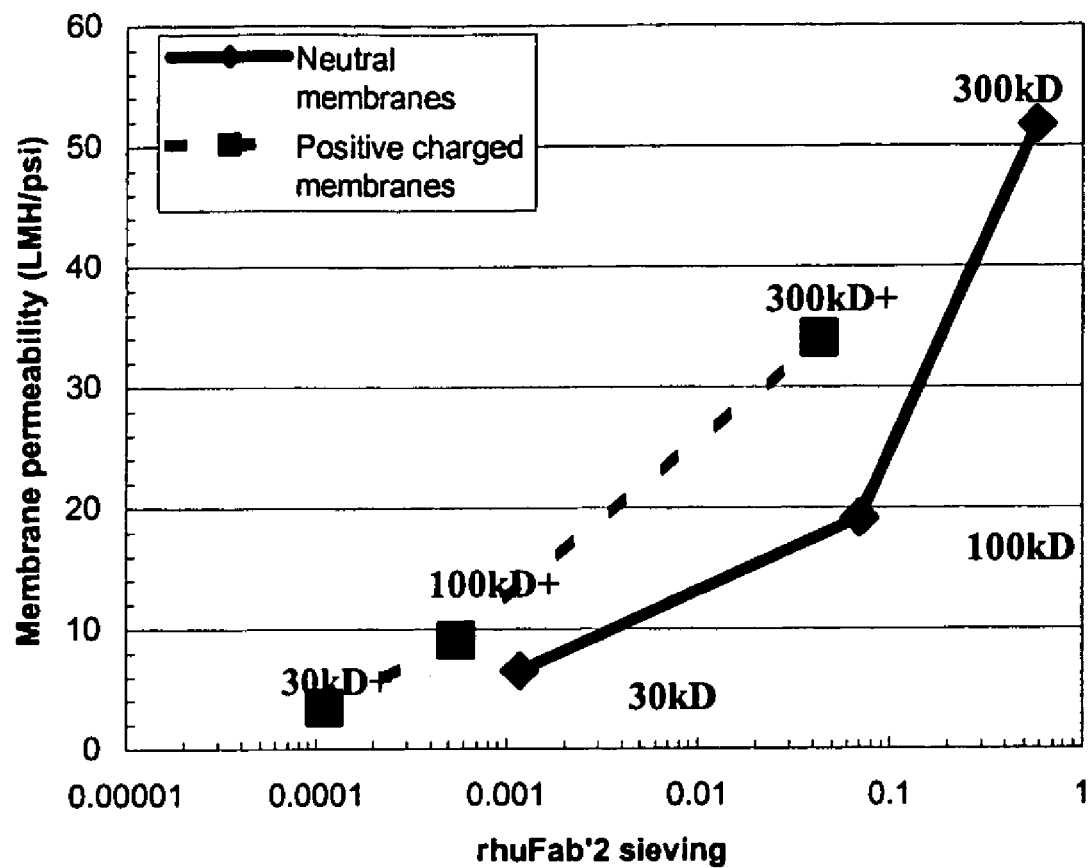
FIG. 8 is a graph of membrane sieving versus permeability for net positively charged target protein rhuFabV2 (anti-CD18, 96 kD MW) on neutral and positively charged membranes having molecular weight cut-offs (MWCO) of 30 kD to 300 kD.

In FIG. 8, the sieving of a positively charged antibody fragment (rhuFab'2, MW~96 kD (ruhuFabV2, anti-CD18, Genentech, Inc.) on neutral and positively charged membranes of MWCOs of 30, 100 and 300 kD is presented. The experiments were performed at a pH of 5.5 and an ionic strength of 1.5 mS/cm. The antibody fragment, having a pI of 8.4, was net positively charged. After applying positive charge on the membrane exterior and pore surfaces, sieving was decreased (increased retention) and sieving values as low as 0.001 were achieved with a positively charged 100 kD membrane as compared to the neutral 100 kD membrane which had a sieving value of approximately 0.1.

Figure 9:
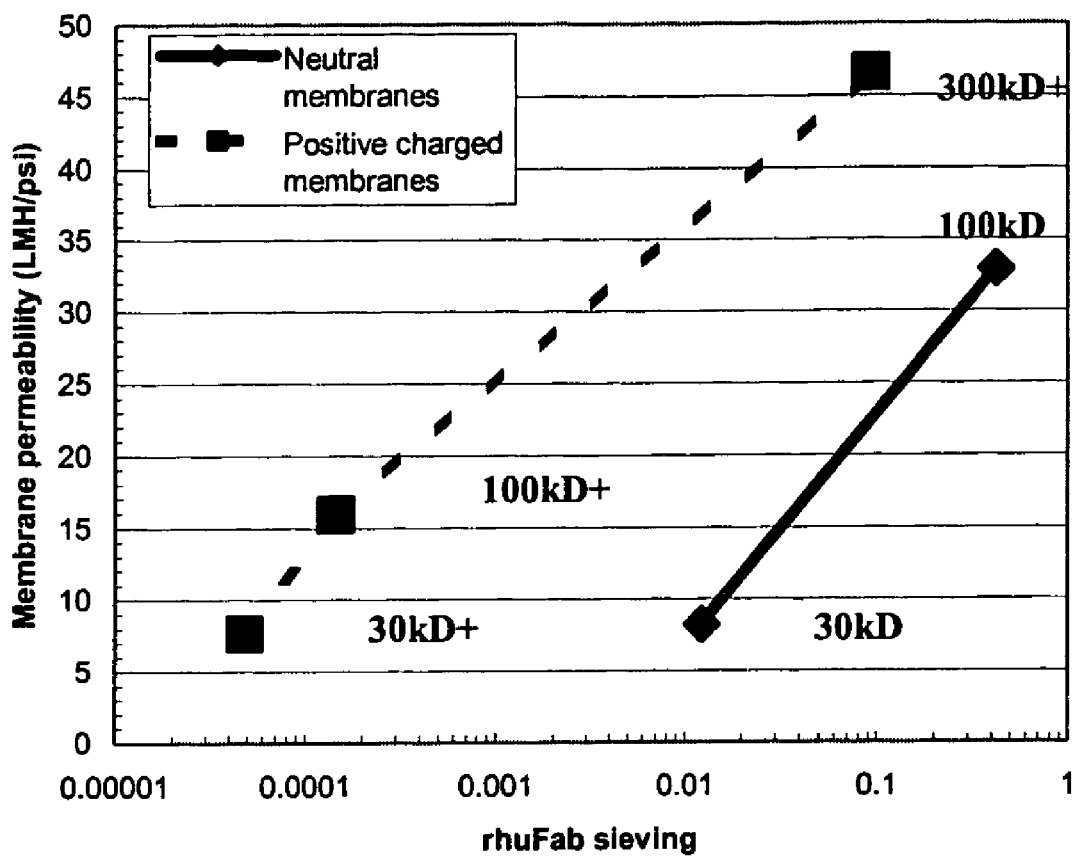
FIG. 9 is a graph of membrane sieving versus permeability for net positively charged target protein rhuFab (anti-VEGF Fab, 48 kD MW) on neutral and positively charged membranes having molecular weight cut-offs (MWCO) of 30 kD to 300 kD.

In FIG. 9, the sieving of a net positively charged antibody fragment (rhuFab anti-VEGF Fab, ~48 kD, Genentech, Inc.) on neutral and positively charged membranes of MWCOs 30, 100 and 300 kD is presented. The rhuFab having a pI of 8.1 was positively charged at the purification conditions of pH of 5.5 and <1 mS/cm. By applying positive charge to the membrane, the sieving on a 30 kD positively charged membrane is more than 100-fold lower than the sieving on a 30 kD neutral membrane of the same Lp (permeabilitiy).

Figure 10:
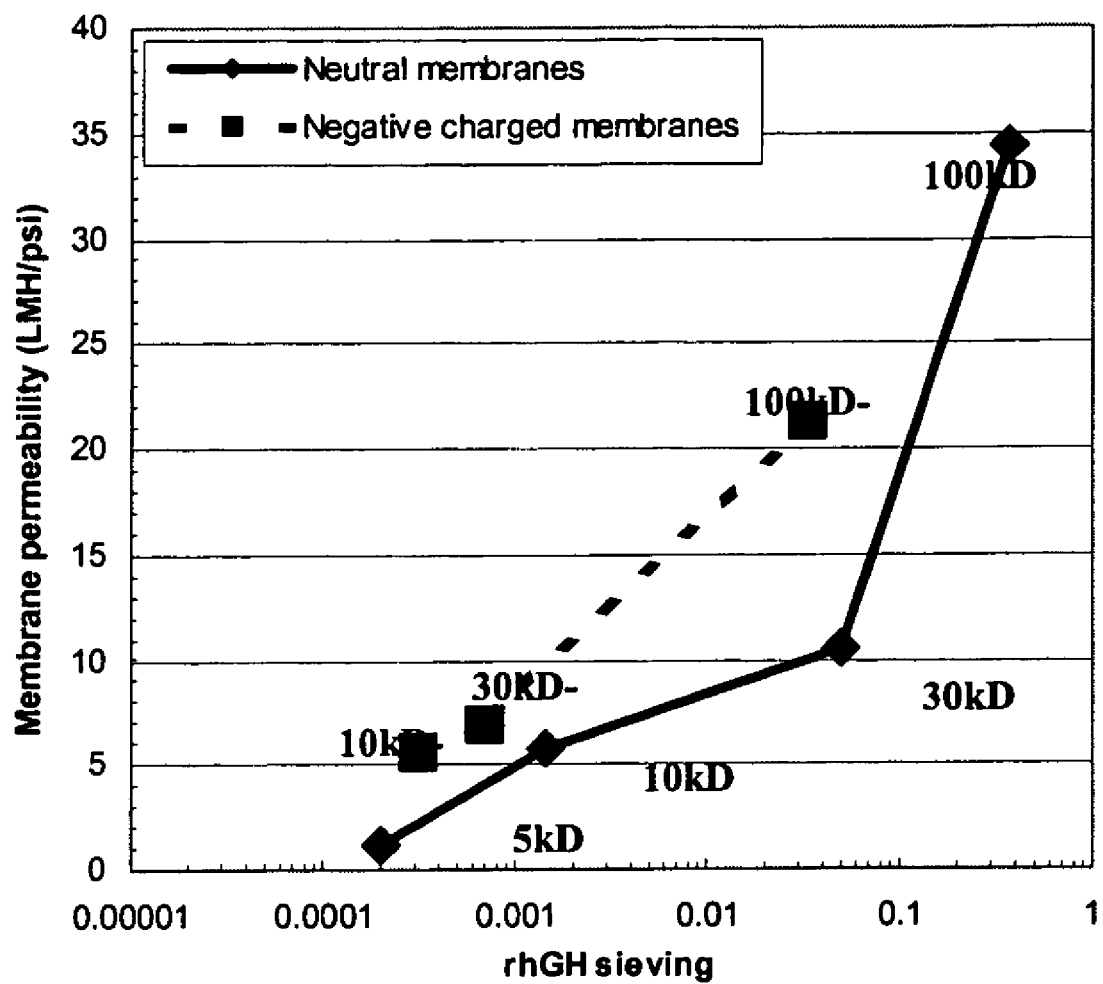
FIG. 10 is a graph of membrane sieving versus permeability for net negatively charged target protein rhGH (22 kD MW) on neutral and negatively charged membranes having molecular weight cut-offs (MWCO) of 5 kD to 100 kD.
Figure 11:
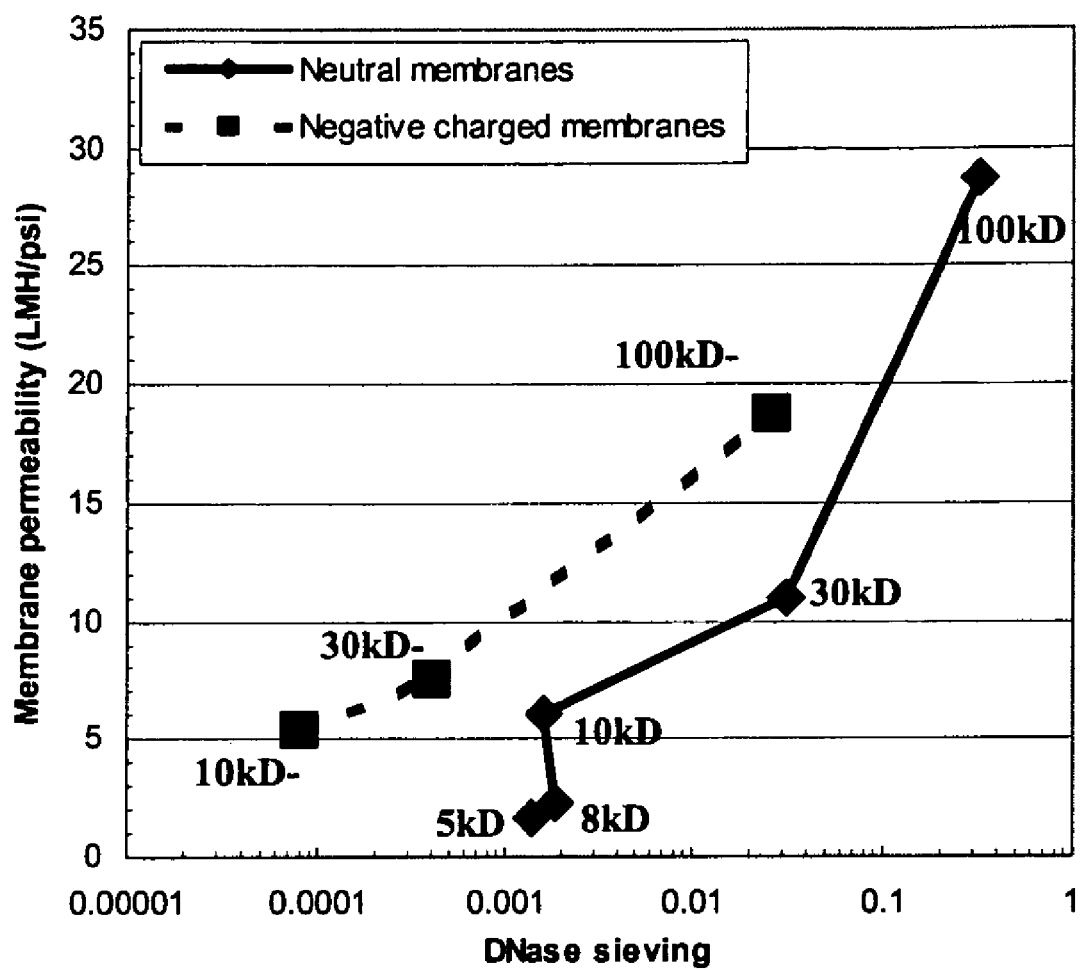
FIG. 11 is a graph of membrane sieving versus permeability for net positively charged target protein DNase (33 kD MW) on neutral and negatively charged membranes having molecular weight cut-offs (MWCO) of 5 kD to 100 kD.

FIGS. 10 and 11 present sieving data for two negatively charged target proteins for various negatively charged and neutral membranes having a range of MWCOs from 5 kD to 100 kD. FIG. 10 presents the sieving of a smaller (~22 kD, pI=5.2 (recombinant human growth hormone, rhGH, Genentech, Inc.)) negatively charged target protein on neutral and negatively charged membranes of molecular weight cut-offs of 5, 10, 30 and 100 kD for purification conditions of pH 7.8 and ionic strength <1 mS/cm. By applying negative charge on the exterior and pore surfaces of a 10 kD membrane, protein sieving was decreased 5-fold with respect to protein sieving on a neutral 10 kD membrane and the entire sieving versus permeability curve was shifted to lower sieving values. Protein sieving on the negative charged 10 kD was comparable with that on a 5 kD neutral membrane but the 10 kD membrane had a 5-fold higher permeability than that of the 5 kD neutral membrane.

Finally, FIG. 11 presents the sieving of a (~33 kD, pI<5 (DNase, Genentech, Inc.)) negatively charged target protein on neutral and negatively charged membranes of MWCOs of 10, 30, 100 kD at a pH7 and an ionic strength of 1.6 mS/cm. By applying the negative charge to the surface and pores of a 10 kD membrane, sieving was decreased 10-fold. Protein sieving was also measured on neutral membranes of MWCOs of 5 kD and 8 kD. The results showed that the charged 10 kD membrane had a better retention (lower sieving) than the 5 kD and 8 kD membranes although its permeability was 5 times higher. For this protein, a 30 kD negatively charged membrane provided approximately 100-fold lower sieving of the target net negative protein, whereas the permeability was 7-fold higher than the permeability of the currently used neutral 5 kD membranes.

Example 6

HPTFF Purification Using Charged Membranes Prepared by the Active Flow Process

A. HPTFF

High Performance Tangential Flow Filtration (HPTFF) is a two-dimensional filtration operation that involves separation of solutes with less than a 10-fold size difference based on both size and charge. A bioprocess mixture of a target protein, anti-HER2 recombinant humanized monoclonal antibody (rhuMAb), and process impurities was partially purified using ion exchange chromatography. The partially purified protein mixture was divided into three equivalent volumes, each 6.9 L and a concentration of about 1.4 g/L of anti-HER2 rhuMAb, prior to further purification by HPTFF. Two of the ion exchange volumes were subjected to different purification conditions in HPTFF Experiment 1 and HPTFF Experiment 2. The resulting pools for HPTFF Experiments 1 and 2 were combined and subjected to additional HPTFF as described in below.

1. Charged Membrane Preparation

Filtration membranes used for HPTFF in this example were Composite Regenerated Cellulose (CRC)-Millipore Ultracel™ (Millipore) with a nominal molecular weight cut-off of 300 kD (PLCMK). CRC300 mini-Pellicon2® membranes pre-packaged in cassette cartridges (Millipore, Bedford, Mass.) were charge-modified as described herein, resulting in the charged cellulose membrane CRC300+ used in the HPTFF studies of this Example. The membrane was cleaned according to a cartridge preparation protocol before the first use to remove any residual storage and shipping solution and to equilibrate the membrane to the appropriate buffer condition. The membrane was chemically modified in its cassette cartridge by passing (3-bromopropyl)trimethyl-ammonium bromide (Sigma-Aldrich, St Louis, Mo.) through the membrane under alkaline conditions. Specifically, the membrane was charged without co-current filtrate flow, at constant filtrate flux of 100 $lm^{-2}h^{-1}$ (LMH), retentate pressure fixed at 10 psig, total recycle with filtrate open mode with 1 L of ligand dissolved in 0.1N NaOH and 0.2 μm filtered. The Lp (permeability) before charging was about 53 $lm^{-2}h^{-1}$/psi in 0.1N NaOH, and the Lp after charging was about 37 $lm^{-2}h^{-1}$/psi in 0.1N NaOH. After charging, the resulting positively charged membrane was cleaned using 0.1N sodium hydroxide, sanitized with 300 ppm of MinnCare™ solution, and stored in 0.1N NaOH. Before each HPTFF experiment, the membrane was flushed with the first diafiltration buffer of the experiment to remove storage solution and was tested for integrity. Membrane permeability was measured using the HPTFF system with co-current filtrate flow at a minimum of three filtrate fluxes.

2. HPTFF Filtration System

HPTFF experiments were performed using a fully automated tangential flow filtration system with the basic configuration. The HPTFF system included a 40-liter stainless steel recycle tank, feed and filtrate flow meters (Admag Model 102 and 105, Johnson Yokogawa Corp., Newman, Ga.) and pressure transducers (Model MSP220-A2, 0–100 psig=0–7 bar, Anderson Instruments, Fultonville, N.Y.). The feed and co-current filtrate flow pumps were positive displacement pumps (Universal 6, Waukesha-Cherry Burrell, Delavan, Wis.) while the diafiltration and filtrate pumps were peristaltic pumps (Model L-7518–62, Cole Parmer, Niles, Ill.). The recycle tank included a temperature probe (Model RIX, −29° C. to 82° C., Moore Industries, Sepulveda, Calif.). All piping was constructed of 316L stainless steel. The retentate pressure control valve was actuated using a steel diaphragm (Model ½ Mikroseal packless control valve, H. D. Baumann, Portsmouth, N.H.), while all other valves were pneumatically actuated with ethylene propylene diene monomer diaphragms (Biotek Model 8836-18-BH, ITT Sherotec, Simi Valley, Calif.). Continuous tank liquid level was measured with a magneto restrictive probe (Model Tempsonics II, MTS, Research Triangle Park, N.C.). Data acquisition and control were performed using proprietary software (Genentech, Inc., South San Francisco, Calif.) using a MycroAdvantage software shell (Moore Products, Springhouse, Pa.).

HPTFF was conducted at a fixed feed flow rate of 323 $l.m^{-2}.h-1$ (volumetric feed flow rate divided by the membrane area) and a retentate pressure of 10 psi. The co-current filtrate flow rate was controlled to reach equal transmembrane pressure at the inlet (feed) and outlet (retentate) of the membrane cassette. The filtrate flux was set at 50 $l.m^{-2}.h^{-1}$ by adjusting the filtrate pump rate. The start-up of HPTFF experiments included a ramp-up of all flow rates in order to minimize the difference between transmembrane pressure at the inlet and outlet of the cassette. The retentate was recycled to the feed tank, while the filtrate was directed to a collection vessel. Feed and filtrate samples were collected in both cases for product and Host Cell Protein (HCP) analysis.

a. HPTFF Experiment 1

After the division of the ion exchange purified protein mixture into equivalent 6.9 L pools, as described above, one of the pools was subjected to HPTFF Experiment 1 using a CRC300+ membrane under the following conditions.

The charged membranes were equilibrated in the first diafiltration buffer for this experiment (see Table 2). The ion exchange pool was diluted to lower the ionic strength and conductivity of the anti-HER2 rhuMAb pool to 2.7 mS/cm, adjusted to a pH of 4.5 and then added to the feed tank. The material in the feed tank was concentrated by removing a portion of the solution. When the bulk volume reached a bulk concentration ($C_b$) of 10 g/L, the solution in the feed tank was subjected to sequential diafiltration steps. With a constant conductivity of 1.5mS/cm, diafiltration was performed with 10 diavolumes at a pH of 4.5 and 5 diavolumes each of pH 5.0, pH 5.5, pH 6.0, and pH 6.5 (Table 2). The yield of purified anti-HER2 rhuMAb target protein was calculated based on the quantifiable product sieving during diafiltration using the following equation: $Y=e^{-NS_T^{arg\ etprotein}}$ where S is the sieving of the target protein and N is the number of diavolumes.

TABLE 2

Experimental conditions and results from HPTFF purification using charged membrane after initial ion exchange chromatography.

| | Concentration $C_b$ (g/L) | Diafiltration pH - N | Yield of target protein (%) | [CHOP*]$_{final}$ ppm |
|---|---|---|---|---|
| Ion Exchange pool | | | | 410 |
| HPTFF Experiment 1 | 10 | 4.5 - 10 | 99% | 21 |
| | | 5.0 - 5 | | |
| | | 5.5 - 5 | | |
| | | 6.0 - 5 | | |
| | | 6.5 - 5 | | |
| HPTFF Experiment 2 | 10 | 4.5 - 10 | 99% | 17 |
| | | 5.5 - 10 | | |
| | | 6.5 - 10 | | |

TABLE 2-continued

Experimental conditions and results from HPTFF purification using charged membrane after initial ion exchange chromatography.

|  | Con-centration $C_b$ (g/L) | Diafiltration pH - N | Yield of target protein (%) | $[CHOP*]_{final}$ ppm |
|---|---|---|---|---|
| Additional HPTFF (Combined pools from HPTFF 1 & 2) | 10 | 6.5 - 40<br>6.0 - 5 | 99% | 2.2 |

*Chinese Hamster Ovary Cell Protein (CHOP) impurity concentration.

The product quality of the recovered pool from the HPTFF Experiment 1 was measured using SDS-PAGE gel electrophoresis, and rhuMAb % intact monomer analysis, and CHOP concentration analysis, to obtain the results of Table 2.

Significant sieving of CHOP impurities (flow through the charged membrane) was observed with CRC300+ with simultaneous low sieving of target protein resulting in no significant loss of anti-HER2 rhuMAb during the charged membrane HPTFF step. The final concentration of CHOP in the recovered pool from HPTFF performed with CRC300+ was quite low at 2 ppm.

b. HPTFF Experiment 2

Another of the ion exchange pools, as described above, having 1.4 mg/ml of rhuMAb, 410 ppm of CHOP, a pH of 5.6 and a conductivity of about 8 mS/cm, was subjected to a HPTFF Experiment 2.

As described above, the CRC300+ membrane was equilibrated in the first diafiltration buffer for this HPTFF Experiment 2 (see Table 2). The ion exchange pool was diluted with water to lower the conductivity to 2.4 mS/cm. The pH was adjusted to pH 4.5 with HCl. The resulting conditioned pool was loaded into the feed tank. In a single operation, the conditioned pool was then concentrated to 10 g/L at pH 4.5, followed by a constant retentate volume diafiltration comprising a specific sequence of diafiltration buffers (Table 2). Three sequences of diafiltration buffers were selected as follows: 10 diavolumes each at a pH of 4.5, 5.5, and 6.5, at a constant conductivity of 1.5 mS/cm. All HPTFF experiments were conducted at a filtrate flux of 50 $l.m^{-2}.h^{-1}$ using a positively charged Pellicon-2® filter mini cassette (a CRC300+ membrane) with a permeability of 36 $l.m^{-2}.h^{-1}/$ psi. The membrane was charge derivatized according to an active flow method of the invention while the membrane was in its cassette.

Upon completion of the HPTFF process performed with CRC300+, analysis of a sample from the recovered pool was by SDS-PAGE, size exclusion chromatography (SEC), and CHOP concentration analysis. Based on these analyses, the purification factors for the HPTFF step was greater than 24 (i.e. 24-fold removal of CHOP) and CHOP removal occurred during both concentration and diafiltration. The CHOP concentration was reduced from 410 ppm (concentration in the material recovered from the Q chromatography column) to 17 ppm (concentration in the material recovered from the HPTFF Experiment 2). No significant filtrate losses were observed.

c. Additional HPTFF on combined material from HPTFF Experiments 1 and 2.

Material recovered after the HPTFF Experiments 1 and 2 was combined and further subjected to additional HPTFF as follows.

As described above, the CRC300+ membrane was equilibrated in the first diafiltration buffer and the combined material was loaded onto the feed tank. The material in the feed tank was subjected to optimal sequential diafiltration steps as follows: 40 diavolumes at pH 6.5 and 1.5 mS/cm, followed by 5 diavolumes at pH 6.0 and 0.3 mS/cm. The additional HPTFF process reduced the concentration of CHOP in the final retentate to 2.2 ppm.

The purification process, involving two steps of non-affinity purification and a third step of HPTFF, resulted in a purity level, as determined by the elimination of CHOP impurities, of about 144,780 ppm of CHOP after a first ion exchange step, of about 410 ppm CHOP after a second ion exchange step, and a final purity of about 17–21 ppm of CHOP after a first HPTFF step. Further purity of about 2.2 ppm of CHOP was achieved by additional HPTFF, thereby demonstrating the ability of charged filtration membranes to offer significant purification while providing high target protein yields.

d. HPTFF Experiment 3

Combination of Non-Affinity Chromatography and Charged Membrane HPTFF Purification The present example involves the purification of recombinant human monoclonal antibody, anti-CD40 rhuMAb, with a molecular weight of 160 kD and a pI of about 9.3 from chinese hamster ovary (CHO) cells. The anti-CD40 rhuMAb was obtained from an industrial scale CHO cell culture process at Genentech (South San Francisco, Calif., USA). After CHO cell culture, the anti-CD40 rhuMAb molecule was partially clarified by centrifugation and normal cell filtration to remove cells and cell debris. The resulting pool consisted of 1.7 mg/ml of anti-CD40 rhuMAb product and approximately 0.4 mg/ml of CHOP.

For purification of anti-CD40 rhuMAb, conditioned harvested cell culture fluid (HCCF) comprising an anti-CD40 rhuMAb product and Chinese Hamster Ovary host cell proteins (CHOP) from CHO cells expressing anti-CD40 rhuMAb was loaded onto an initial cation exchange chromatography column (S) (SP-Sepharose Fast Flow™ Resin, Amersham Biosciences) to remove host cell proteins or CHO proteins (CHOP), variants, DNA impurities and aggregates. Elutions from the S column were pooled (S pool) and subjected to a second anion exchange chromatography column (Q) (Q-Sepharose Fast Flow™ resin, Amersham Biosciences, Piscataway, N.J.) to remove CHOP, DNA impurities and target protein aggregates. The flow-through from the Q column (Q pool) was further subjected to a third process of HPTFF for further removal of CHOP, variants and small molecules.

A. Non-Affinity Chromatography

1. Methods

For preparation of the non-affinity chromatography columns, bind-and-elute SP-Sepharose and flow-through Q-Sepharose were each packed into preparative scale columns. The operating conditions for each chromatography column are presented in Table 3.

TABLE 3

Non-affinity Chromatography Operating Conditions

| Resin | Resin Type | Mode of Operation | Buffers | Load Conditioning |
|---|---|---|---|---|
| SP Sepharose Fast Flow ™ (Amersham Biosciences, Piscataway, NJ) | Cation exchange (S) | Non-specific bind and elute | 20 mM MES, 50 mM NaAcetate, pH 6.5 | <7.0 mS/cm pH 6.5 |
| Q Sepharose Fast Flow ™ (Amersham Biosciences, NJ) | Anion exchange (Q) | Flow-through | 25 mM Tris, 50 mM NaCl, pH 8 | <8 mS/cm pH 8 |

The HCCF was conditioned by diluting the HCCF to a conductivity of less than 7 mS/cm with water and adjusting the HCCF to a pH of 6.5 with acetic acid and filtered through a 0.22 μm filter. The SP-Sepharose column was equilibrated with 4 column volumes (CVs) of the column buffer (Table 3) and loaded to approximately 30 grams of rhuMAb/liter of resin for a total of about 13 grams of rhuMAb at a flow rate of 150 cm/h. After loading the conditioned HCCF onto the SP-Sepharose column, the column was washed with 5 CVs of wash buffer (20 mM HEPES, 35 mM NaAcetate, pH 8.0) followed by 3 CVs of column buffer (Table 4). Elutions were made with a 10 CV gradient elution from the column buffer to the elution buffer 20 mM MES, 140 mM NaAcetate, pH 6.5, with the eluant collected at an absorbance of from 0.1 to 0.5 AU at 280 nm. The chromatography resin was regenerated in a 0.5 M NaOH solution and further stored in 0.1 M NaOH.

The SP-Sepharose pool (SP pool) was conditioned by diluting the S pool to a conductivity of approximately 7.5 mS/cm with water and adjusted to a pH of 8 with NaOH. The conditioned S pool, having a total mass of about 9 grams, was then filtered through a 0.22 μm filter. The filtered conditioned SP pool was loaded onto a Q-Sepharose column that was equilibrated with 5 CVs of the column buffer (see Table 3). The flow-through was collected at 0.2-0.2 AU at 280nm and the flow-through was pooled (Q pool). The Q-Sepharose chromatography resin was regenerated in a 0.5 M NaOH solution and further stored in 0.1 M NaOH.

2. Analysis

Figure 12:
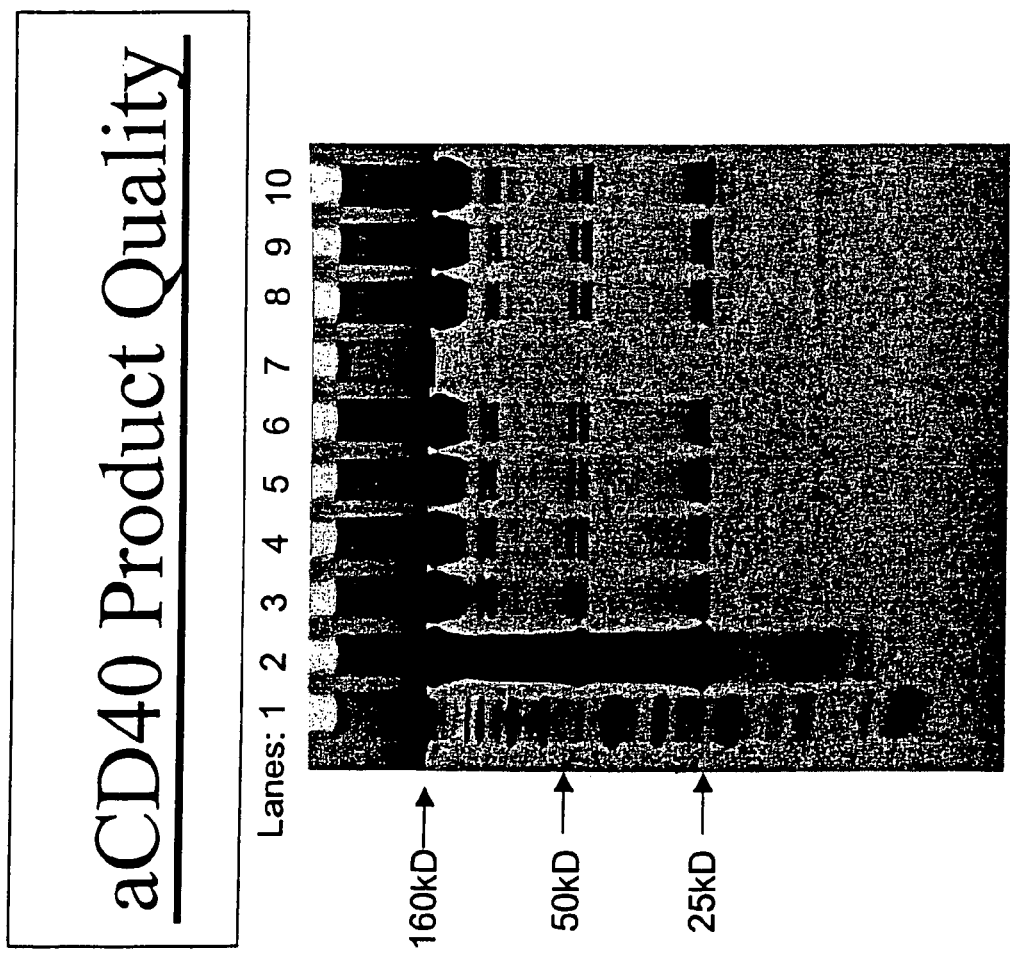
FIG. 12 shows a gel in which the product quality of samples from Example 6d (HPTFF Experiment 3), a combined ion exchange-charged membrane HPTFF purification of anti-CD40, were analyzed. Lane 1: standards; Lane 2: HCCF; Lane 3: S pool; Lane 4: Q pool; Lane 5: HPTFF; Lane 6: HPTFF—buffer flush; Lane 7: blank; Lane 8: SP pool after affinity step; Lane 9: Q pool (with affinity step); Lane 10: anti-CD40 reference material (with affinity step).

The amount of anti-CD40 rhuMAb in each pool following a purification step of the process, i.e. in the HCCF and in the pools from the purification process, was determined by an HPLC analysis based on Protein-A immunoaffinity chromatography. CHOP concentration was determined using the enzyme-linked immunosorbent (ELISA) assay. Upon completion of the S and Q chromatography, samples from pools were subjected to SDS-PAGE analysis (FIG. 12, lanes 3 and 4, respectively). The Q pool was diluted to lower the ionic strength and conductivity of the RhuMAb pool to 1.8 mS/cm, adjusted to a pH of 4.5 (a pH at which anti-CD40 rhuMAb is positively charged) and then added to the feed tank of an HPTFF system. The material in the feed tank was subjected to concentration by removal of a portion of the solution. When the bulk volume reached a bulk concentration ($C_b$) of 10 g/L, the solution in the feed tank was subjected to sequential diafiltration steps in HPTFF using a positively charged CRC300+membrane prepared by passing (3-bromopropyl)trimethylammonium bromide through a CRC300 membrane in its cassette cartridge as described in Example 6, herein. With a constant conductivity of 1.5 mS/cm, diafiltration was performed with 5 diavolumes each at a pH 4.5 and pH 5.5, followed by 20 diavolumes at pH 6.5, followed by 10 diavolumes at pH 7.0 (Table 4). The yield was calculated based on the quantifiable product sieving during diafiltration using the following equation: $Y = e^{-NS_T \, arg \, eprotein}$ where S is the sieving of the target protein and N the number of diavolumes.

The product quality of the recovered pool from this HPTFF Experiment 3 was subjected to analysis, including SDS-PAGE gel electrophoresis (FIG. 12, lane 5), rhuMAb % intact monomer analysis and CHOP concentration analysis (Table 4). DNA concentration was evaluated according to the Total DNA Assay using the Molecular Devices Threshold DNA assay kit (Molecular Devices, Santa Clara, Calif.) (Table 4). The Total DNA Assay is specific for single-stranded DNA, which is obtained from the sample via denaturation by heat. The single-stranded DNA is labeled with binding proteins, which are covalently bound to urease and streptavidin, and form a DNA complex. The DNA complex is filtered through a biotin coated nitrocellulose membrane known as a "stick." The biotin on the membrane reacts with streptavidin in the DNA complex, capturing the complex. The stick is placed in the Threshold Reader, which contains the substrate, urea. The enzymatic reaction between urea and urease (in the DNA complex) changes the local pH of the substrate solution. A silicon sensor records a change in surface potential, which is proportional to the pH change. The rate of change in surface potential is proportional to the amount of DNA. Quantification of samples is determined by comparison to DNA standards. Samples are diluted so that the DNA content falls within the reporting range of the standard curve (10–400 pg/mL).

TABLE 4

Experimental conditions and results from charged membrane HPTFF

| | Concentration $C_b$ (g/L) | Diafiltration pH–N | Yield (%) | [CHOP] (ppm) | [DNA] (ppm) |
|---|---|---|---|---|---|
| Q pool | | | 96% | 15 | 15 |
| HPTFF pool | 10 | 4.5–5 5.5–5 6.5–20 7.0–10 | 99% | <0.6 | <0.6 |

Significant sieving of CHOP was observed with CRC300+ without any significant loss of anti-CD40 rhuMAb. CHOP removal occurred during both concentration and diafiltration. The CHOP concentration was reduced from 15 ppm (concentration in the material recovered from the Q chromatography column) to to less than 0.6 ppm within the first 20 diavolumes (concentration in the protein pool in the feed tank). The removal of CHOP impurities was confirmed by measuring the concentration in the material recovered from this HPTFF Experiment 3 (see Table 4). No significant filtrate losses were observed.

The purification process, involving two steps of non-affinity purification and a third step of charged membrane HPTFF, resulted in a purity level, as determined by (1) the elimination of CHOP impurities, of about 530 ppm of CHOP after S purification, of about 15 ppm CHOP after Q purification, and a final purity of about less than 0.6 ppm of CHOP, and by (2) the elimination of DNA impurities, of about 0.1 ppm of CHOP after S purification, of about less than 0.01 ppm DNA after Q purification, and a final purity of about less than 0.006 ppm of DNA (see Table 5). In addition, the electrophoresis analysis illustrated the comparable purity of the non-affinity final pool to that a conventional pool obtained using an affinity step (FIG. 12).

TABLE 5

CHO host cell protein quantification and purity analysis of anti-CD40 rhuMAb feedstream in purification processes

| Purification Step | [CHOP] (ppm) | % intact rhuMAb monomer (measured by SEC) | [DNA] (ppm) |
|---|---|---|---|
| HCCF | 240,000 | — | >5441 |
| S pool | 530 | — | 0.1 |
| Q pool | 15 | — | <0.01 |
| HPTFF pool | <0.6 | 99.5% | <0.006 |
| Control Process: (using steps: ProA-S-Q-UFDF) | 3 | 99.5% | <0.003 |

The foregoing written specification is considered sufficient to enable one skilled in the art to practice the invention. The present invention is not to be limited in scope by the examples provided, since the examples are illustrative of certain aspects of the invention and any compositions or methods that are functionally equivalent are within the scope of this invention. Indeed, various modifications of the invention in addition to those shown and described herein will become apparent to those skilled in the art from the foregoing description and fall within the scope of the appended claims.

What is claimed is:

1. A filtration membrane comprising a charged compound covalently attached to a hydroxyl group on a precursor cellulose membrane,
   wherein membrane pore size distribution of the filtration membrane comprising the charged compound is reduced relative to the precursor membrane,
   wherein, for the filtration membrane comprising the charged compound and a protein solute having like charge, solute sieving is improved by at least 1.5 fold relative to the precursor membrane, and
   wherein, for the filtration membrane comprising the charged compound, a sieving versus permeability curve is shifted to lower sieving values, but the permeability values remain substantially the same, relative to a curve obtained with the precursor membrane.

2. The membrane of claim 1, wherein the precursor membrane is a composite regenerated cellulose membrane.

3. The filtration membrane of claim 1, the charged compound comprising a linker.

4. The filtration membrane of claim 3, wherein the linker comprises a heteroatom selected from the group consisting essentially of N, O, S, and P.

5. The filtration membrane of claim 3, wherein the linker is selected from the group consisting essentially of an alkyl chain of from 1 to 20 carbon atoms, a branched alkyl chain of from 1 to 20 carbon atoms, a ring structure, a carbohydrate, a saccharide, a dextran, and an amino acid.

6. The filtration membrane of claim 1, wherein the charge is positive.

7. The filtration membrane of claim 6, wherein the charged compound comprises a charged moiety selected from the group consisting of an amine and a quaternary ammonium ion.

8. The filtration membrane of claim 1, wherein the charge is negative.

9. The filtration membrane of claim 8, wherein the charged compound comprises a charged moiety selected from the group consisting of an acid, a sulfonic acid, and a carboxylic acid.

10. The filtration membrane of claim 8, wherein the covalently attached charged compound is attached by an ether linkage.

11. The filtration membrane of claim 1, wherein the precursor membrane is selected from the group consisting of cellulose, composite regenerated cellulose (CRC), cellulose diacetate and triacetate, cellulose nitrate, and cellulose diacetate/cellulose nitrate blends.

* * * * *